(12) United States Patent
Cottard et al.

(10) Patent No.: US 7,771,492 B2
(45) Date of Patent: *Aug. 10, 2010

(54) COMPOSITIONS FOR OXIDATION DYEING KERATIN FIBERS COMPRISING AT LEAST ONE THICKENING POLYMER COMPRISING AT LEAST ONE FATTY CHAIN AND AT LEAST ONE FATTY ALCOHOL CHOSEN FROM MONOGLYCEROLATED FATTY ALCOHOLS AND POLYGLYCEROLATED FATTY ALCOHOLS

(75) Inventors: François Cottard, Levallois-Perret (FR); Christine Rondeau, Sartrouville (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/390,879

(22) Filed: Feb. 23, 2009

(65) Prior Publication Data

US 2009/0260164 A1 Oct. 22, 2009

Related U.S. Application Data

(63) Continuation of application No. 10/959,486, filed on Oct. 7, 2004, now abandoned, which is a continuation of application No. 09/750,716, filed on Jan. 2, 2001, now abandoned.

(30) Foreign Application Priority Data

Dec. 30, 1999 (FR) .................................. 99 16757

(51) Int. Cl.
*A61Q 5/10* (2006.01)
(52) U.S. Cl. ....................... 8/405; 8/406; 8/410; 8/411; 8/412; 8/421; 8/540; 8/552; 8/554; 8/562; 8/611
(58) Field of Classification Search ............ 8/405, 8/406, 408, 410, 411, 412, 421, 540, 552, 8/554, 562, 611
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle et al. |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,528,378 A | 10/1950 | Mannhelmer |
| 2,781,354 A | 2/1957 | Mannheimer |
| 2,961,347 A | 2/1957 | Mannheimer |
| 3,206,462 A | 9/1965 | McCarty |
| 3,227,615 A | 1/1966 | Korden |
| 3,589,578 A | 6/1971 | Kamphausen et al. |
| 3,632,559 A | 1/1972 | Matter et al. |
| 3,836,537 A | 9/1974 | Boerwinkle et al. |
| 3,849,548 A | 11/1974 | Grand |
| 3,874,870 A | 4/1975 | Green et al. |
| 3,893,803 A | 7/1975 | Kaiser |
| 3,910,862 A | 10/1975 | Barabas et al. |
| 3,912,808 A | 10/1975 | Sokol |
| 3,915,921 A | 10/1975 | Schlatzer, Jr. |
| 3,917,817 A | 11/1975 | Vanlerberghe et al. |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,003,699 A | 1/1977 | Rose et al. |
| 4,005,193 A | 1/1977 | Green et al. |
| 4,013,787 A | 3/1977 | Vanerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,131,576 A | 12/1978 | Iovine et al. |
| 4,157,388 A | 6/1979 | Christiansen |
| 4,166,894 A | 9/1979 | Schaper |
| 4,172,887 A | 10/1979 | Vanlerberghe et al. |
| 4,197,865 A | 4/1980 | Jacquet et al. |
| 4,223,009 A | 9/1980 | Chakrabarti |

(Continued)

FOREIGN PATENT DOCUMENTS

DE  23 59 399  11/1973

(Continued)

OTHER PUBLICATIONS

English language Derwent Abstract of EP 0 557 203, Aug. 25, 1993.

(Continued)

*Primary Examiner*—Eisa B Elhilo
(74) *Attorney, Agent, or Firm*—Finnegan, Henderson, Farabow, Garrett & Dunner, LLP

(57) ABSTRACT

Compositions for oxidation dyeing of keratin fibers, in particular human keratin fibers such as hair, comprising, in a dyeing medium, at least one oxidation dye, at least one thickening polymer comprising at least one fatty chain and at least one fatty alcohol chosen from monoglycerolated and polyglycerolated fatty alcohols. Processes comprising such oxidation dyeing compositions.

74 Claims, No Drawings

U.S. PATENT DOCUMENTS

| | | | |
|---|---|---|---|
| 4,228,259 A | 10/1980 | Kalopissis et al. | |
| 4,277,581 A | 7/1981 | Vanlerberghe et al. | |
| 4,314,807 A | 2/1982 | Grollier et al. | |
| 4,349,532 A | 9/1982 | Vanlerberghe et al. | |
| 4,390,689 A | 6/1983 | Jacquet et al. | |
| 4,509,949 A | 4/1985 | Huang et al. | |
| 4,555,246 A | 11/1985 | Grollier et al. | |
| 4,591,610 A | 5/1986 | Grollier | |
| 4,702,906 A | 10/1987 | Jacquet et al. | |
| 4,719,099 A | 1/1988 | Grollier et al. | |
| 4,719,282 A | 1/1988 | Nadolsky et al. | |
| 4,761,273 A | 8/1988 | Grollier et al. | |
| 4,820,308 A | 4/1989 | Madrange et al. | |
| 4,839,166 A | 6/1989 | Grollier et al. | |
| 4,842,849 A | 6/1989 | Grollier et al. | |
| 4,943,430 A | 7/1990 | Hefford et al. | |
| 4,970,066 A | 11/1990 | Grollier et al. | |
| 4,996,059 A | 2/1991 | Grollier et al. | |
| 5,009,880 A | 4/1991 | Grollier et al. | |
| 5,061,289 A | 10/1991 | Clausen et al. | |
| 5,139,037 A | 8/1992 | Grollier et al. | |
| 5,196,189 A | 3/1993 | Jacquet et al. | |
| 5,298,240 A | 3/1994 | Schröder et al. | |
| 5,380,340 A | 1/1995 | Neunhoeffer et al. | |
| 5,538,517 A * | 7/1996 | Samain et al. | 8/423 |
| 5,567,421 A | 10/1996 | Cotteret et al. | |
| 5,735,908 A | 4/1998 | Cotteret et al. | |
| 5,766,576 A | 6/1998 | Löwe et al. | |
| 5,851,237 A * | 12/1998 | Anderson et al. | 8/409 |
| 5,938,792 A | 8/1999 | Lang et al. | |
| 5,976,195 A | 11/1999 | de la Mettrie et al. | |
| 5,984,975 A * | 11/1999 | Lagrange et al. | 8/412 |
| 5,989,295 A * | 11/1999 | de la Mettrie et al. | 8/406 |
| 6,099,592 A | 8/2000 | Vidal et al. | |
| 6,106,578 A | 8/2000 | Jones | |
| 6,117,436 A | 9/2000 | Flemming et al. | |
| 6,143,286 A | 11/2000 | Bhambhani et al. | |
| 6,156,077 A | 12/2000 | Shibata et al. | |
| 6,214,326 B1 | 4/2001 | Dupuis | |
| 6,251,145 B1 | 6/2001 | De La Mettrie et al. | |
| 6,294,158 B1 | 9/2001 | Dupuis | |
| 6,312,677 B1 | 11/2001 | Millequant et al. | |
| 6,423,101 B1 | 7/2002 | Yaker et al. | |
| 6,551,359 B1 | 4/2003 | Lang et al. | |
| 6,576,024 B1 | 6/2003 | Lang et al. | |
| 6,592,633 B2 | 7/2003 | Lang et al. | |
| 6,602,303 B2 * | 8/2003 | Laurent et al. | 8/405 |

FOREIGN PATENT DOCUMENTS

| | | |
|---|---|---|
| DE | 32 12 198 | 10/1982 |
| DE | 213 835 | 3/1983 |
| DE | 38 43 892 | 12/1988 |
| DE | 41 33 957 | 10/1991 |
| DE | 195 43 988 | 11/1995 |
| DE | 197 14 370 | 4/1997 |
| DE | 197 57 509 | 12/1997 |
| EP | 0 080 976 | 6/1983 |
| EP | 0 122 324 | 10/1984 |
| EP | 0 173 109 | 3/1986 |
| EP | 0 216 479 | 4/1987 |
| EP | 0 223 572 | 5/1987 |
| EP | 0 337 354 | 10/1989 |
| EP | 0 384 415 | 8/1990 |
| EP | 0 490 053 | 6/1992 |
| EP | 0 557 203 | 8/1993 |
| EP | 0 634 163 | 1/1995 |
| EP | 0 640 334 | 3/1995 |
| EP | 0 673 641 | 9/1995 |
| EP | 0 716 846 | 6/1996 |
| EP | 0 827 738 | 3/1998 |
| EP | 0 960 617 | 12/1999 |
| FR | 1.400.366 | 4/1965 |
| FR | 1.492.597 | 7/1967 |
| FR | 1.583.363 | 10/1969 |
| FR | 2.077.143 | 10/1971 |
| FR | 2.080.759 | 11/1971 |
| FR | 2.162.025 | 7/1973 |
| FR | 2.190.406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 236 434 | 7/1977 |
| FR | 2 368 508 | 5/1978 |
| FR | 2 283 660 | 10/1978 |
| FR | 2 393 573 | 1/1979 |
| FR | 2 413 907 | 3/1979 |
| FR | 2 428 437 | 1/1980 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 598 611 | 11/1987 |
| FR | 2 733 749 | 11/1996 |
| FR | 2 750 048 | 12/1997 |
| FR | 2 773 472 | 1/1998 |
| FR | 2 773 475 | 7/1999 |
| GB | 1026978 | 4/1966 |
| GB | 1153 196 | 5/1969 |
| GB | 2 188 948 | 10/1987 |
| JP | 2-19576 | 1/1990 |
| JP | 9-110659 | 4/1997 |
| WO | WO 94/08969 | 4/1994 |
| WO | WO 94/08970 | 4/1994 |
| WO | WO 96/15765 | 5/1996 |
| WO | WO 98/56333 | 12/1998 |
| WO | WO 99/17727 | 4/1999 |

OTHER PUBLICATIONS

English language Derwent Abstract of EP 0 080 976, Jun. 8, 1983.
English language Derwent Abstract of FR 2.077.143, Oct. 15, 1971.
English language Derwent Abstract of FR 2.080.759, Sep. 20, 1971.
English language Derwent Abstract of FR 2 320 330, Mar. 4, 1977.
English language Derwent Abstract of FR 2 336 434, Jul. 22, 1977.
English language Derwent Abstract of FR 2 750 048, Dec. 26, 1997.
English language Derwent Abstract of FR 2 773 472, Jan. 13, 1998.
English language Derwent Abstract of DE 197 14 370, Apr. 8, 1997.
English language Derwent Abstract of DE 197 57 509, Dec. 23, 1997.
English language Derwent Abstract of JP 9-110659, Apr. 28, 1997.
Fonnum et al., "Associative thickeners. Part 1: Synthesis, rheology and aggregation behavior", Colloid & Polymer Science, vol. 271, No. 4, Apr. 1993, pp. 380-389.
Porter et al. Handbook of Surfactants, 1991, pp. 117-178.
Co-pending U.S. Appl. No. 09/750,718; Title: Compositions for Oxidation Dyeing Keratin Fibers Comprising At Least One Thickening Polymer Comprising At Least One Oxidation Dye, At Least One Thickening Polymer Comprising At Least One Fatty Chain, and At Least One Fatty Alcohol Comprising More Than Twenty Inventors: François Cottard et al. U.S. Filing Date: Jan. 2, 2001.
Co-pending U.S. Appl. No. 09/750,757; Title: Compositions for Oxidation Dyeing Keratin Fibers Comprising At Least One Fatty Alcohol Having More Than Twenty Carbon Atoms and At Least One Oxyalkylenated Nonionic Surfactant With an HLB Greater Than 5 Inventors: François Cottard et al. U.S. Filing Date: Jan. 2, 2001.
Co-pending U.S. Appl. No. 09/750,717; Title: Compositions for Oxidation Dyeing Keratin Fibers Comprising At Least Two Particular Quaternary Polyammoniums and Uses Thereof Inventors: François Cottard et al. U.S. Filing Date: Jan. 2, 2001.
English language Abstract of JP 2-19576, dated Jan. 23, 1990.
Griffin, W.C., "Calculation of HLB Values of Non-Ionic Surfactants," J. Soc. Cosm. Chem. vol. 5, pp. 249-256 (1954).

Notice of Allowance mailed Mar. 26, 2002, in U.S. Appl. No. 09/750,718.
Notice of Allowance mailed Oct. 2, 2003, in U.S. Appl. No. 09/750,757.
Notice of Allowance mailed Sep. 7, 2005, in U.S. Appl. No. 09/750,717.
Office Action mailed Apr. 5, 2002, in U.S. Appl. No. 09/750,717.
Office Action mailed Feb. 10, 2005, in U.S. Appl. No. 09/750,717.
Office Action mailed Jan. 23, 2002, in U.S. Appl. No. 09/750,757.
Office Action mailed Jul. 21, 2004, in U.S. Appl. No. 09/750,717.
Office Action mailed Jul. 28, 2003, in U.S. Appl. No. 09/750,717.
Office Action mailed Jun. 19, 2002, in U.S. Appl. No. 09/750,757.
Office Action mailed Nov. 21, 2002, in U.S. Appl. No. 09/750,717.
Orecchioni, A. et al., "Notions de HLB et de HLB Critique," GALENCIA 5 Agents de Surface & Emulsions, 1983, pp. 152-195.

* cited by examiner

COMPOSITIONS FOR OXIDATION DYEING KERATIN FIBERS COMPRISING AT LEAST ONE THICKENING POLYMER COMPRISING AT LEAST ONE FATTY CHAIN AND AT LEAST ONE FATTY ALCOHOL CHOSEN FROM MONOGLYCEROLATED FATTY ALCOHOLS AND POLYGLYCEROLATED FATTY ALCOHOLS

This is a continuation of application Ser. No. 10/959,486, filed Oct. 7, 2004, now abandoned which is a continuation of application Ser. No. 09/750,716, filed Jan. 2, 2001, now abandoned which claims the benefit of French Patent Application No. 99 16757, filed Dec. 30, 1999, the contents of all of which are incorporated herein by reference.

The present invention relates to cosmetic compositions for oxidation dyeing of keratin fibers, such as human keratin fibers like hair, comprising, in a dyeing medium, (1) at least one oxidation dye, (2) at least one thickening polymer comprising at least one fatty chain, and (3) at least one fatty alcohol chosen from monoglycerolated and polyglycerolated fatty alcohols.

It is known to dye keratin fibers, for example human hair, with dyeing compositions comprising oxidation dye precursors, generally called "oxidation bases." Representative oxidation bases include ortho- and para-phenylenediamines, ortho- and para-aminophenols, and heterocyclic bases.

Oxidation dye precursors are compounds initially only slightly colored or not colored that develop their dyeing power in the hair in the presence of oxidizing agents, leading to the formation of colored compounds. The formation of these colored compounds results either from oxidative condensation of the "oxidation bases" with themselves, or oxidative condensation of the "oxidation bases" with color-modifying compounds, or "couplers," which are generally present in the dyeing compositions used in oxidation dyeing. Representative couplers include meta-phenylenediamines, meta-aminophenols, meta-diphenols, and certain heterocyclic compounds.

The variety of compositions that can be employed in oxidation coloration, chosen from oxidation bases, oxidation couplers and mixtures of oxidation bases and couplers, can contribute to a pallet very rich in color.

Traditional thickeners, which can provide a gelling effect when diluted by water and/or surfactants, have been used conventionally to localize the dye product as applied on hair, so that the dye product does not touch the face or the area outside the area to be dyed. Such thickeners, chosen as appropriate, for example include crosslinked polyacrylic acid, hydroxyethylcelluloses, certain polyurethanes, waxes or mixtures of nonionic surfactants having an HLB (Hydrophilic Lipophilic Balance).

However, the inventors have observed that the above-mentioned thickening systems may impede a result of intense and chromatic shades of low selectivity and good fastness and a good cosmetic condition to the treated hair. However, it has also been observed that the ready-to-use dyeing compositions comprising known oxidation dye(s) and thickening systems tend to result in imprecise application of such compositions and/or a decrease in viscosity over time.

The inventors have discovered that it is possible to obtain ready-to-use oxidation dyeing compositions that resist running and tend to remain well-confined to the site of application. Additionally, such compositions may favor more intense and more chromatic (radiant) shades, while exhibiting low selectivities and good fastness toward chemical agents (shampoo, permanent waving and the like) and/or natural agents (light, perspiration and the like), and while offering the hair good cosmetic properties. The inventors have discovered that it is possible to obtain at least one of the aforementioned characteristics by formulating a ready-to-use cosmetic dyeing composition comprising (1) at least one oxidation dye, (2) at least one thickening polymer comprising at least one fatty chain, and (3) at least one fatty alcohol chosen from monoglycerolated and polyglycerolated fatty alcohols.

The inventors have discovered that it is possible to obtain at least one of the aforementioned characteristics by formulating a ready-to-use cosmetic dyeing composition comprising (1) at least one oxidation dye, (2) at least one thickening polymer comprising at least one fatty chain, and (3) at least one fatty alcohol chosen from monoglycerolated and polyglycerolated fatty alcohols.

The inventors have also discovered that said compositions comprising (1) at least one oxidation dye, (2) at least one thickening polymer comprising at least one fatty chain, and (3) at least one fatty alcohol chosen from monoglycerolated and polyglycerolated fatty alcohols tend to be stable upon storage.

At least one of these discoveries forms the basis of the present invention.

One subject of the present invention is thus a cosmetic composition for oxidation dyeing keratin fibers, such as human keratin fibers like hair, comprising, in a dyeing medium (1) at least one oxidation dye, (2) at least one thickening polymer comprising at least one fatty chain, and (3) at least one fatty alcohol chosen from monoglycerolated and polyglycerolated fatty alcohols.

Another subject of the invention relates to a ready-to-use cosmetic composition for oxidation dyeing keratin fibers comprising, in a dyeing medium, (1) at least one oxidation dye, (2) at least one thickening polymer comprising at least one fatty chain, (3) at least one fatty alcohol chosen from monoglycerolated and polyglycerolated fatty alcohols, and (4) at least one oxidizing agent. The term "ready-to-use composition" is understood to mean, for the purposes of the present invention, a composition intended to be applied immediately to the keratin fibers, either stored as it is before use or obtained from the mixture of two or more compositions.

The invention also relates to a method for oxidation dyeing keratin fibers, such as human keratin fibers like hair, comprising applying to said keratin fibers at least one composition (A) comprising, in a dyeing medium:
  at least one oxidation dye,
  at least one thickening polymer comprising at least one fatty chain, and
  at least one fatty alcohol chosen from monoglycerolated and polyglycerolated fatty alcohols, developing the color with the aid of at least one composition (B) comprising at least one oxidizing agent, wherein said at least one oxidizing composition (B) is combined at the time of use with said at least one composition (A) or said at least one oxidizing composition (B) is applied sequentially to said at least one composition (A) without intermediate rinsing.

A variation of the above-described method is a method for oxidation dyeing keratin fibers, such as human keratin fibers like hair, comprising:
  applying to said keratin fibers at least one dyeing composition comprising, in a dyeing medium, at least one oxidation dye and at least one fatty alcohol chosen from monoglycerolated and polyglycerolated fatty alcohols, and optionally comprising at least one thickening polymer comprising at least one fatty chain, developing the color with the aid of at least one oxidizing composition comprising at least one oxidizing agent and an effective quantity of at least one thickening polymer comprising at least one fatty chain, wherein said at least one oxidizing composition is combined at the time of use with said at least one dyeing composition or wherein said at least one oxidizing composition is applied sequentially to said at least one dyeing composition without intermediate rinsing.

One embodiment of the invention relates to multicompartment dyeing devices or "kits" for oxidation dyeing keratin fibers, such as human keratin fibers like hair.

A kit according to the invention comprises at least two compartments, wherein:

a first compartment comprises (1) at least one oxidation dye, (2) at least one thickening polymer comprising at least one fatty chain, and (3) at least one fatty alcohol chosen from monoglycerolated and polyglycerolated fatty alcohols, and a second compartment comprises at least one oxidizing agent.

According to one variant, another kit comprises at least two compartments, wherein:

a first compartment comprises at least one oxidation dye and at least one fatty alcohol chosen from monoglycerolated and polyglycerolated fatty alcohols, and optionally comprises at least one thickening polymer comprising at least one fatty chain and a second compartment comprises at least one oxidizing agent and an effective quantity of at least one thickening polymer comprising at least one fatty chain.

According to another variant, a three-compartment kit comprises:

a first compartment comprising at least one oxidation dye and at least one fatty alcohol chosen from monoglycerolated and polyglycerolated fatty alcohols, and optionally comprising at least one thickening polymer comprising at least one fatty chain, a second compartment comprising at least one thickening polymer comprising at least one fatty chain and a third compartment comprising at least one oxidizing agent and optionally comprising at least one thickening polymer comprising at least one fatty chain.

At Least One Fatty Alcohol Chosen from Monoglycerolated and Polyglycerolated Fatty Alcohols The expression at least one (as used herein, "at least one" means one or more and thus includes mixtures and combinations) fatty alcohol chosen from monoglycerolated and polyglycerolated fatty alcohols is understood to mean compounds of the following formula:

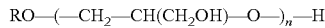

in which:

R is chosen from linear and branched, saturated and unsaturated groups comprising from 8 to 40 carbon atoms, such as from 10 to 30 carbon atoms;

n is a number ranging from 1 to 30, such as from 1 to 10.

Representative monoglycerolated and polyglycerolated fatty alcohols include, for example, lauryl alcohol comprising 4 mol of glycerol (INCI name: POLYGLYCERYL-4 LAURYL ETHER), oleyl alcohol comprising 4 mol of glycerol (INCI name: POLYGLYCERYL-4 OLEYL ETHER), oleyl alcohol comprising 2 mol of glycerol (INCI name: POLYGLYCERYL-2 OLEYL ETHER), cetearyl alcohol comprising 2 mol of glycerol, cetearyl alcohol comprising 6 mol of glycerol, oleocetyl alcohol comprising 6 mol of glycerol and octadecanol comprising 6 mol of glycerol.

The fatty alcohol may represent a mixture of fatty alcohols in the same way that the value of n represents a statistical value, which means that in a commercial product, for example, several species of polyglycerolated fatty alcohols can coexist in the form of a mixture.

The at least one fatty alcohol chosen from monoglycerolated and polyglycerolated fatty alcohols can be present in an amount ranging for example from 0.01% to 30% by weight relative to the total weight of the composition, such as from 0.05% to 20% by weight relative to the total weight of the composition and further such as from 0.1% to 15% by weight relative to the total weight of the composition.

At Least One Thickening Polymer Comprising at Least One Fatty Chain

The at least one thickening polymer comprising at least one fatty chain according to the invention can be chosen from nonionic, anionic and cationic thickening polymers comprising at least one fatty chain.

(i) Anionic Thickeners

Such anionic thickening polymers comprising at least one fatty chain can be chosen from:

(I) anionic polymers comprising at least one hydrophilic unit and at least one allyl ether unit comprising at least one fatty chain, for example said anionic polymers wherein said at least one hydrophilic unit comprises at least one ethylenic unsaturated anionic monomeric residue, such as vinylcarboxylic acid and further such as at least one monomeric residue chosen from acrylic acid and methacrylic acid residues, and wherein said at least one allyl ether unit comprising at least one fatty chain corresponds to the monomeric residue resulting from the monomer of formula (I):

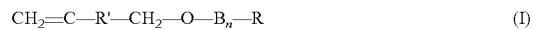

in which R' is chosen from H and $CH_3$, B is chosen from ethyleneoxy groups, n is chosen from zero and integers ranging from 1 to 100, R is a hydrocarbon group chosen from alkyl, arylalkyl, aryl, alkylaryl and cycloalkyl groups, comprising from 8 to 30 carbon atoms, such as from 10 to 24, and further such as from 12 to 18 carbon atoms. One embodiment of the invention comprises at least one allyl ether unit of the monomeric resudue resulting from the monomer of formula (I), wherein R' is H, n is equal to 10, and R is a stearyl ($C_{18}$) group.

Representative anionic amphiphilic polymers of this type are described and prepared, according to a method of emulsion polymerization, in patent EP-0,216,479, the disclosure of which is incorporated by reference herein.

As used herein, the term "lower alkyl" means an alkyl chosen from saturated and unsaturated, branched and unbranched $C_1$-$C_6$ alkyl groups.

Representative anionic thickening polymers comprising at least one fatty chain include for example polymers formed from 20% to 60% by weight of at least one monomer chosen from acrylic acid and methacrylic acid, 5% to 60% by weight of $C_1$-$C_6$ alkyl(meth)acrylates, 2% to 50% by weight of allyl ether comprising at least one fatty chain of formula (I), and up to 1% by weight of a crosslinking agent chosen from well known copolymerizable polyethylenic unsaturated monomers such as diallyl phthalate, allyl (meth)acrylate, divinylbenzene, (poly)ethylene glycol dimethacrylate and methylenebisacrylamide.

One embodiment could comprise at least one anionic thickening polymer chosen from crosslinked terpolymers of methacrylic acid, ethyl acrylate, and polyethylene glycol (10 EO) stearyl alcohol ether (Steareth 10), such as the products sold by the company ALLIED COLLOIDS under the names SALCARE SC 80 and SALCARE SC 90, which are aqueous emulsions comprising 30% of a crosslinked terpolymer of methacrylic acid, of ethyl acrylate and of steareth-10-allyl ether (40/50/10).

Anionic thickening polymers comprising at least one fatty chain can also be chosen from:
(II) anionic polymers comprising at least one hydrophilic unit of the olefinic unsaturated carboxylic acid type and at least one hydrophobic unit of the ($C_{10}$-$C_{30}$)alkyl ester of unsaturated carboxylic acid type.

Such polymers are chosen from polymers comprising:
at least one hydrophilic unit formed from olefinic unsaturated carboxylic acid monomers of formula (II):

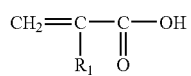
(II)

in which $R_1$ is chosen from H, $CH_3$, and $C_2H_5$, (which corresponds with acrylic acid, methacrylic acid and ethacrylic acid units), and
at least one hydrophobic unit formed from ($C_{10}$-$C_{30}$)alkyl esters of unsaturated carboxylic acid monomers of formula (III):

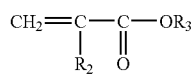
(III)

in which $R_2$ is chosen from H, $CH_3$, and $C_2H_5$, (which corresponds with acrylate, methacrylate and ethacrylate units) and $R_3$ is chosen from saturated and unsaturated, branched and unbranched $C_{10}$-$C_{30}$ alkyl groups. In one embodiment, for example, $R_2$ is chosen from H (acrylate units) and $CH_3$ (methacrylate units) and $R_3$ is chosen from $C_{12}$-$C_{22}$ alkyl groups.

($C_{10}$-$C_{30}$)alkyl esters of unsaturated carboxylic acids in accordance with the invention include for example lauryl acrylate, stearyl acrylate, decyl acrylate, isodecyl acrylate, dodecyl acrylate, lauryl methacrylate, stearyl methacrylate, decyl methacrylate, isodecyl methacrylate, and dodecyl methacrylate.

Anionic polymers of this type are for example described and prepared according to U.S. Pat. Nos. 3,915,921 and 4,509,949, the disclosures of which are incorporated by reference herein.

Anionic thickening polymers comprising at least one fatty chain that can be used include polymers formed from a mixture of monomers comprising:
(i) acrylic acid,
(ii) at least one ester of formula (III) described above wherein $R_2$ is chosen from H and $CH_3$, and $R_3$ is chosen from alkyl groups comprising from 12 to 22 carbon atoms, and
(iii) at least one crosslinking agent chosen from well known copolymerizable polyethylenic unsaturated monomers such as diallyl phthalate, allyl (meth)acrylate, divinylbenzene, (poly)ethylene glycol dimethacrylate and methylenebisacrylamide.

Representative anionic thickening polymers comprising at least one fatty chain that can be used include (i) polymers comprising 95% to 60% by weight of acrylic acid monomeric residue (hydrophilic unit), 4% to 40% by weight of $C_{10}$-$C_{30}$ alkyl acrylate monomeric residue (hydrophobic unit), and 0% to 6% by weight of crosslinking polymerizable monomeric residue, and (ii) polymers comprising 98% to 96% by weight of acrylic acid monomeric residue (hydrophilic unit), 1% to 4% by weight of $C_{10}$-$C_{30}$ alkyl acrylate monomeric residue (hydrophobic unit) and 0.1% to 0.6% by weight of crosslinking polymerizable monomeric residue such as those described above.

Among the above polymers, the products sold by the company GOODRICH under the trade names PEMULEN TR1, PEMULEN TR2, and CARBOPOL 1382 can be used. One embodiment could employ at least one polymer chosen from PEMULEN TR1, and the product sold by the company S.E.P.P.I.C. under the name COATEX SX.

Anionic thickening polymers comprising at least one fatty chain can also be chosen from:
(III) terpolymers formed from maleic anhydride/$C_{30}$-$C_{38}$ α-olefin/alkyl maleate such as the product (maleic anhydride/$C_{30}$-$C_{38}$ α-olefin/isopropyl maleate copolymer) sold under the name PERFORMA V 1608 by the company NEWPHASE TECHNOLOGIES,
(IV) acrylic terpolymers formed from:
(a) 20% to 70% by weight of a carboxylic acid with α,β-monoethylenic unsaturation
(b) 20% to 80% by weight of a nonsurfactant monomer with α,β-monoethylenic unsaturation different from (a)
(c) 0.5% to 60% by weight of a nonionic monourethane which is the product of the reaction of a monohydric surfactant with a monoisocyanate with monoethylenic unsaturation such as acrylic terpolymers described in patent application EP-A-0,173,109, the disclosure of which is incorporated by reference herein, and more particularly acrylic terpolymers described therein in Example 3, namely a methacrylic acid/methyl acrylate/dimethyl metaisopropenyl benzyl isocyanate of ethoxylated (40 EO) behenyl alcohol terpolymer in 25% aqueous dispersion,
(V) copolymers formed from at least two monomers, wherein at least one of said at least two monomers is chosen from a carboxylic acid with α,β-monoethylenic unsaturation, an ester of a carboxylic acid with α,β-monoethylenic unsaturation, and an oxyalkylenated fatty alcohol, and
(VI) copolymers formed from at least three monomers, wherein at least one of said at least three monomers is chosen from a carboxylic acid with α,β-monoethylenic unsaturation, at least one of said at least three monomers is chosen from an ester of a carboxylic acid with α,β-monoethylenic unsaturation and at least one of said at least three monomers is chosen from an oxyalkylenated fatty alcohol.

Additionally, these compounds can also comprise, as monomer, a carboxylic acid ester comprising an α,β-monoethylenic unsaturation and a $C_1$-$C_4$ alcohol. By way of example of this type of compound, there may be mentioned ACULYN 22 sold by the company ROHM and HAAS, which is an oxyalkylenated stearyl methacrylate/ethyl acrylate/methacrylic acid terpolymer.

(ii) Nonionic Thickeners

Nonionic thickening polymers comprising at least one fatty chain according to the invention can be chosen from:
(1) celluloses modified by at least one group comprising at least one fatty chain such as:
hydroxyethylcelluloses modified by at least one group comprising at least one fatty chain such as alkyl, arylalkyl and alkylaryl groups and further such as alkyl, arylalkyl and alkylaryl groups wherein said alkyl groups comprise from 8-22 carbon atoms, such as the product NATROSOL PLUS GRADE 330 CS($C_{16}$ alkyls) sold by the company AQUALON, and the product BERMOCOLL EHM 100 sold by the company BEROL NOBEL, hydroxyethylcelluloses modified by at least one polyalkylene glycol ether of alkylphenol group, such as the product AMERCELL POLYMER HM-1500 (polyethylene glycol (15) ether of nonylphenol) sold by the company AMERCHOL;

(2) hydroxypropylguars modified by at least one group comprising at least one fatty chain such as the product ESAFLOR HM 22 ($C_{22}$ alkyl chain) sold by the company LAMBERTI, the products RE 210-18 ($C_{14}$ alkyl chain) and RE 205-1 ($C_{20}$ alkyl chain) sold by the company RHONE POULENC (Succeeded by RHODIA CHIMIE);

(3) copolymers formed from vinylpyrrolidone and at least one hydrophobic monomer comprising at least one fatty chain such as for example:
  the products ANTARON V216 and GANEX V216 (vinylpyrrolidone/hexadecene copolymer) sold by the company I.S.P., and
  the products ANTARON V220 and GANEX V220 (vinylpyrrolidone/eicosene copolymer) sold by the company I.S.P.;

(4) copolymers formed from at least one $C_1$-$C_6$ alkyl methacrylate and at least one amphiphilic monomer comprising at least one fatty chain and copolymers formed from at least one $C_1$-$C_6$ alkyl acrylate and at least one amphiphilic monomer comprising at least one fatty chain such as for example the oxyethylenated stearyl acrylate/methyl acrylate copolymer sold by the company GOLDSCHMIDT under the name ANTIL 208;

(5) copolymers formed from at least one hydrophilic methacrylate and at least one hydrophobic monomer comprising at least one fatty chain and copolymers formed from at least one hydrophilic acrylate and at least one hydrophobic monomer comprising at least one fatty chain such as for example the polyethylene glycol methacrylate/lauryl methacrylate copolymer;

(6) polyether-polyurethanes comprising in their chain both hydrophilic sequences which are most often of a polyoxyethylenated nature and hydrophobic sequences which may be chains chosen from aliphatic chains, cycloaliphatic chains, and aromatic chains;

(7) polymers comprising an aminoplast ether backbone possessing at least one fatty chain, such as the compounds PURE THIX provided by the company SUD-CHEMIE.

Nonionic thickening polymers can additionally include polyether-polyurethanes comprising at least two lipophilic (i.e., hydrophobic) hydrocarbon chains, comprising from 6 to 30 carbon atoms, separated by a hydrophilic sequence, it being possible for the hydrocarbon chains to be chosen from pendant chains and chains at the end of a hydrophilic sequence. One embodiment may comprise at least one pendant chain. In addition, the polymer may comprise a hydrocarbon chain at least one end of a hydrophilic sequence.

Representative polyether-polyurethanes useful in the present invention may be polyblocks, such as in triblock form. The hydrophobic sequences may be at each end of the chain (for example: triblock copolymer with hydrophilic central sequence) and optionally both at the ends and in the chain (polyblock copolymer for example). These same polymers may also be in the form of graft units or may be star-shaped.

The nonionic polyether-polyurethanes comprising at least one fatty chain may be triblock copolymers whose hydrophilic sequence is a polyoxyethylenated, chain comprising from 50 to 1000 oxyethylenated groups. Certain nonionic polyether-polyurethanes comprise a urethane bond between the hydrophilic sequences.

By extension, those whose hydrophilic sequences are linked by other chemical bonds to the lipophilic sequences are also included among the nonionic polyether-polyurethanes comprising at least one fatty chain.

Representative nonionic polyether-polyurethanes comprising at least one fatty chain include Rhéolate 205 comprising a urea function sold by the company RHEOX and Rhéolate 208, 204 and 212, as well as Acrysol RM 184, Aculyn 44 and Aculyn 46 from the company ROHM and HAAS [ACULYN 46 is a polycondensate of polyethylene glycol comprising 150 or 180 mol of ethylene oxide, stearyl alcohol and methylene-bis(4-cyclohexylisocyanate) (SMDI), at 15% by weight in a maltodextrin (4%) and water (81%) matrix; ACULYN 44 is a polycondensate of polyethylene glycol comprising 150 or 180 mol of ethylene oxide, decyl alcohol and methylenebis(4-cyclohexylisocyanate) (SMDI), at 35% by weight in a propylene glycol (39%) and water (26%) mixture].

There may also be mentioned the product ELFACOS T210 comprising a $C_{12}$-$C_{14}$ alkyl chain and the product ELFACOS T212 comprising a $C_{18}$ alkyl chain from AKZO.

The product DW 1206B from RHOM & HAAS comprising a $C_{20}$ alkyl chain and with a urethane bond, sold at 20% dry matter content in water, may also be used.

It is also possible to use solutions and dispersions of these polymers for example in water and for example in an aqueous-alcoholic medium. By way of example of such polymers, there may be mentioned Rhéolate 255, Rhéolate 278 and Rhéolate 244 sold by the company RHEOX. It is also possible to use the product DW 1206F and DW 1206J provided by the company ROHM & HAAS.

Representative polyether-polyurethanes that can be used according to the invention include polyether-polyurethanes described in the article by G. Formum, J. Bakke and Fk. Hansen—Colloid Polym. Sci 271, 380, 389 (1993), the disclosure of which is incorporated by reference herein.

(iii) Cationic Thickeners

As used herein, "cationic thickener" refers to polymers chosen from polymers comprising at least one cationic group and polymers comprising at least one group which can be ionized to form cationic groups.

Representative cationic thickening polymers comprising at least one fatty chain used in the present invention can be chosen from quaternized cellulose derivatives and polyacrylates with noncyclic amine-containing side groups.

Such quaternized cellulose derivatives can be chosen from:
  quaternized celluloses modified by groups comprising at least one fatty chain, such as at least one group chosen from alkyl, arylalkyl and alkylaryl groups comprising at least 8 carbon atoms,
  quaternized hydroxyethylcelluloses modified by at least one group comprising at least one fatty chain, such as at least one group chosen from alkyl, arylalkyl and alkylaryl groups comprising at least 8 carbon atoms.

In one embodiment, said alkyl groups carried by the above quaternized celluloses and hydroxyethylcelluloses comprise from 8 to 30 carbon atoms and the aryl groups are chosen from phenyl, benzyl, naphthyl and anthryl groups.

There may be mentioned as examples of quaternized alkylhydroxyethylcelluloses comprising at least one $C_8$-$C_{30}$ fatty chain the products QUATRISOFT LM 200, QUATRISOFT LM-X 529-18-A, QUATRISOFT LM-X 529-18B ($C_{12}$ alkyl) and QUATRISOFT LM-X 529-8 ($C_{18}$ alkyl) marketed by the company AMERCHOL and the products CRODACEL QM, CRODACEL QL ($C_{12}$ alkyl) and CRODACEL QS ($C_{18}$ alkyl) marketed by the company CRODA.

Representative polyacrylates with amine-containing side groups, quaternized and otherwise, comprise for example hydrophobic groups of the steareth 20 type (polyoxyethylenated stearyl alcohol (20)).

As examples of polyacrylates with amine-containing side groups, there may be mentioned the polymers 8781-121B or 9492-103 from the company NATIONAL STARCH.

One embodiment of the oxidation dyeing composition according to the invention may comprise at least one nonionic thickening polymer comprising at least one fatty chain.

The anionic, nonionic and cationic at least one thickening polymer comprising at least one fatty chain is generally present in an amount ranging for example from 0.01% to 10% by weight relative to the total weight of the dyeing composition, such as from 0.1% to 5% by weight relative to the total weight of the dyeing composition.

Oxidation Dyes

The at least one oxidation dye which can be used according to the present invention is chosen from oxidation bases, and oxidation couplers. In one embodiment, the compositions can comprise at least one oxidation base.

The oxidation bases usable in the context of the present invention are chosen from those conventionally known as oxidation dyes. Representative oxidation dyes include ortho- and para-phenylenediamines, double bases, ortho- and para-aminophenols and heterocyclic bases as well as their addition salts with an acid.

For example, the following oxidation bases may be used:

(I) para-phenylenediamines chosen from compounds of formula (I), and their acid addition salts:

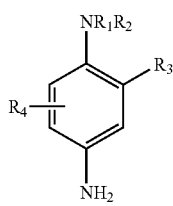

(I)

wherein:
- $R_1$ is chosen from hydrogen, $C_1$-$C_4$ alkyl groups, monohydroxy($C_1$-$C_4$ alkyl) groups, polyhydroxy($C_2$-$C_4$ alkyl) groups, ($C_1$-$C_4$)alkoxy($C_1$-$C_4$)alkyl groups, phenyl groups, 4'-aminophenyl groups, and $C_1$-$C_4$ alkyl groups substituted with at least one group chosen from nitrogen-containing groups,
- $R_2$ is chosen from hydrogen, $C_1$-$C_4$ alkyl groups, monohydroxy($C_1$-$C_4$ alkyl) groups, polyhydroxy($C_2$-$C_4$ alkyl) groups, ($C_1$-$C_4$)alkoxy($C_1$-$C_4$)alkyl groups, and $C_1$-$C_4$ alkyl groups substituted with a nitrogen-containing group;
- $R_1$ and $R_2$ may also form, together with the nitrogen atom to which they are bonded, a 5- or 6-membered nitrogen-containing heterocycle ring, optionally substituted with at least one group chosen from alkyl groups, hydroxyl groups and ureido groups;
- $R_3$ is chosen from hydrogen, halogens, such as chlorine, $C_1$-$C_4$ alkyl groups, sulfo groups, carboxyl groups, monohydroxy($C_1$-$C_4$ alkyl) groups, hydroxy($C_1$-$C_4$ alkyoxy) groups, acetylamino($C_1$-$C_4$ alkoxy) groups, mesylamino($C_1$-$C_4$ alkoxy) groups, and carbamoylamino($C_1$-$C_4$ alkoxy) groups;
- $R_4$ is chosen from hydrogen, halogens, and $C_1$-$C_4$ alkyl groups.

Suitable nitrogen-containing groups of formula (I) above may, for example, be chosen from amino, ($C_1$-$C_4$) monoalkylamino, ($C_1$-$C_4$)dialkylamino, ($C_1$-$C_4$)trialkylamino, monohydroxy($C_1$-$C_4$)alkylamino, imidazolinium, and ammonium groups.

Representative para-phenylenediamines of formula (I) above which may be used include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 2-methyl-1-N-β-hydroxyethyl-para-phenylenediamine and their acid addition salts.

In other embodiments of the present invention, para-phenylenediamines of formula (I) above can, for example, be chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, and their acid addition salts.

According to the invention, "double bases" is understood to mean the compounds comprising at least two aromatic rings on which at least one functional group chosen from amino groups and hydroxyl groups are carried.

(II) double bases chosen from compounds comprising at least two aromatic rings substituted with at least one group chosen from amino and hydroxyl groups. Such double bases may be chosen from compounds of formula (II), and their acid addition salts:

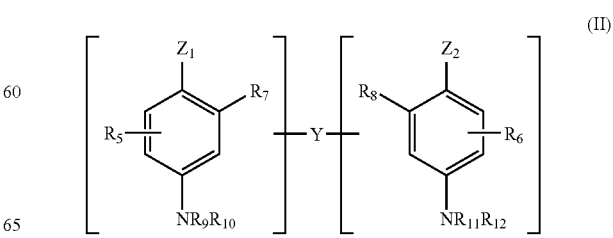

(II)

wherein:
Z$_1$ and Z$_2$, which may be identical or different, are each chosen from hydroxyl groups, and —NH$_2$ groups, optionally substituted with a group chosen from C$_1$-C$_4$ alkyl groups, and linkers Y;

linker Y is chosen from linear and branched, divalent alkylene groups comprising from 1 to 14 carbon atoms, optionally interrupted by, or optionally terminating with, at least one entity chosen from nitrogen-containing groups and heteroatoms such as oxygen, sulfur, and nitrogen, and optionally substituted with at least one group chosen from hydroxyl groups, and C$_1$-C$_6$ alkoxy groups;

R$_5$ and R$_6$, which may be identical or different, are each chosen from hydrogen, halogens, C$_1$-C$_4$ alkyl groups, monohydroxy(C$_1$-C$_4$ alkyl) groups, polyhydroxy(C$_2$-C$_4$ alkyl) groups, amino(C$_1$-C$_4$ alkyl) groups, and linkers Y;

R$_7$, R$_8$, R$_9$, R$_{10}$, R$_{11}$ and R$_{12}$, which may be identical or different, are each chosen from hydrogen, linkers Y, and C$_1$-C$_4$ alkyl groups;

provided that said compounds of formula (II) comprise only one linker Y per molecule.

Suitable nitrogen-containing groups of formula (II) include mono(C$_1$-C$_4$)alkylamino, (C$_1$-C$_4$)dialkylamino, (C$_1$-C$_4$)trialkylamino, monohydroxy(C$_1$-C$_4$)alkylamino, imidazolinium and ammonium groups.

Representative double bases of formula (II) include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl) tetramethylenediamine, N,N'-bis(β-hydroxyethyl)-N,N '-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,5-dioxaoctane, and their acid addition salts.

In another embodiment of the invention, the double bases of formula (II) may be chosen from N,N'-bis(β-hydroxyethyl)-N,N'-bis(4'-aminophenyl)-1,3-diaminopropanol, 1,8-bis(2,5-diaminophenoxy)-3,5-dioxaoctane, and their acid addition salts.

(III) para-aminophenols chosen from compounds of formula (III), and their acid addition salts:

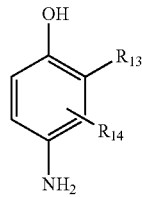

(III)

wherein:
R$_{13}$ is chosen from hydrogen, halogens, such as fluorine, C$_1$-C$_4$ alkyl groups, monohydroxy(C$_1$-C$_4$ alkyl) groups, (C$_1$-C$_4$)alkoxy(C$_1$-C$_4$)alkyl groups, amino(C$_1$-C$_4$ alkyl), and hydroxy(C$_1$-C$_4$)alkylamino(C$_1$-C$_4$ alkyl) groups;

R$_{14}$ is chosen from hydrogen, halogens, such as fluorine, C$_1$-C$_4$ alkyl groups, monohydroxy(C$_1$-C$_4$ alkyl) groups, polyhydroxy(C$_2$-C$_4$ alkyl) groups, amino(C$_1$-C$_4$ alkyl) groups, cyano(C$_1$-C$_4$ alkyl) groups, and (C$_1$-C$_4$)alkoxy (C$_1$-C$_4$)alkyl groups.

Representative para-aminophenols of formula (III) above include para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and their acid addition salts.

(IV) ortho-aminophenols chosen, for example, from 2-aminophenol, 2-amino-1-hydroxy-5-methylbenzene, 2-amino-1-hydroxy-6-methylbenzene, 5-acetamido-2-aminophenol, and their acid addition salts.

(V) heterocyclic bases chosen, for example, from pyridine derivatives, pyrimidine derivatives, pyrazole derivatives, pyrazolo-pyrimidine derivatives, and their acid addition salts.

Representative pyridine derivatives include 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their acid addition salts. Some of the aforementioned pyridine derivatives have been described, for example in the patents GB 1,026,978 and GB 1,153,196, the disclosures of which are incorporated by reference herein.

Representative pyrimidine derivatives include 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and their acid addition salts. Some of the aforementioned pyrimidine derivatives have been described, for example in German Patent DE 2,359,399, Japanese Patents JP 88-169,571 and JP 91-10659, and Patent Application WO 96/15765, the disclosures of which are incorporated by reference herein.

Representative pyrazolo-pyrimidine derivatives include those described, for example, in the patent application FR-A-2 750 048, the disclosure of which is incorporated by reference herein. Such pyrazolo-pyrimidine derivatives include pyrazolo[1,5-a]pyrimidines, such as
pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)-(2-hydroxyethyl)amino]ethanol;
2-[(7-aminopyrazolo[1,5-a]pyrimidin-3-yl)-(2-hydroxyethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5, N7,N7-tetramethylpyrazolo[1,5-a]pyrimidine-3,7-diamine;
3-amino-5-methyl-7-imidazolylpropylaminopyrazolo[1,5-a]pyrimidine; their salts, such as their acid addition salts, and their tautomeric forms when a tautomeric equilibrium exists.

Representative pyrazole derivatives include 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1- ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and their acid addition salts. Some of the aforementioned pyrazole derivatives have been described, for example in Patents DE 3,843,892, DE 4,133, 957 and Patent Applications WO 94/08969, WO 94/08970, FR-A-2,733,749 and DE 195 43 988, the disclosures of which are incorporated by reference herein.

In accordance with the present invention, the oxidation bases are generally present in an amount ranging for example from 0.0005% to 12% by weight relative to the total weight of the composition, such as from 0.005% to 8% by weight relative to the total weight of the composition.

Suitable couplers which may be used in the dyeing process of the invention include couplers conventionally used in oxidation dyeing compositions. Such couplers can be chosen, for example, from meta-phenylenediamines, meta-aminophenols, meta-diphenols, naphthols, sesamol and its derivatives, heterocyclic couplers, such as, for example, indole derivatives, indoline derivatives, pyridine derivatives, pyrazolotriazole derivatives, pyrazolones, indazoles, benzimidazoles, benzothiazoles, benzoxazoles, 1,3-benzodioxoles, quinolines and their acid addition salts.

Representative couplers include 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, 1-amino-2-methoxy-4,5-methylenedioxybenzene, 2-amino-3-hydroxypyridine, 3,6-dimethylpyrazolo[3,2-c]-1,2,4-triazole, 2,6-dimethylpyrazolo[1,5-b]-1,2,4-triazole, and their acid addition salts.

When these couplers are present, they are generally present in an amount ranging for example from 0.0001% to 10% by weight relative to the total weight of the composition, such as from 0.005% to 5% by weight relative to the total weight of the composition.

Generally, the acid addition salts of the oxidation bases and couplers can be chosen from hydrochlorides, hydrobromides, sulfates, tartrates, lactates and acetates.

The compositions according to the invention may also comprise at least one direct dye. Representative direct dyes which can be used in the present invention include direct dyes that have conventionally been used in direct dyeing compositions and lighting direct dyeing compositions. For example, the dyes can be chosen from neutral, cationic, and anionic nitro dyes, neutral, cationic, and anionic anthraquinone dyes, and neutral, cationic, and anionic azo dyes. Generally, the direct dyes are present in amounts ranging for example from 0.001% to 20% by weight of the total weight of the composition, such as for example from 0.01% to 10% by weight of the total weight of the composition.

In one embodiment of the invention, namely within the ready-to-use composition, said at least one composition (A) and said at least one composition (B) can further comprise at least one polymer chosen from cationic and amphoteric polymers, such as substantive polymers.

Cationic Polymers

As used herein, "cationic polymer" refers to polymers chosen from polymers comprising at least one cationic group and polymers comprising at least one group which can be ionized to form cationic groups.

Representative cationic polymers which may be used in accordance with the present invention include any of those already known to improve at least one cosmetic property of hair, such as, for example, those described in patent application EP-A-0 337 354 and in French patent applications FR-A-2 270 846, 2 383 660, 2 598 611, 2 470 596 and 2 519 863, the disclosures of which are incorporated herein by reference.

According to the present invention, the at least one cationic polymer may be chosen from polymers comprising at least one unit, wherein said at least one unit comprises at least one group chosen from primary amine groups, secondary amine groups, tertiary amine groups and quaternary amine groups, wherein said at least one group forms part of the polymer skeleton, or is carried by at least one lateral substituent on said polymer skeleton.

According to the present invention, the at least one cationic polymer has a number-average molecular mass generally ranging for example from 500 to $5 \times 10^6$, such as from $1 \times 10^3$ to $3 \times 10^6$.

The at least one cationic polymer may, for example, be chosen from polymers of quaternary polyammonium type, polymers of polyamino amide type and polymers of polyamine type. Such types of polymers are known in the art. They are for example described in French patents Nos. 2, 505, 348 and 2, 542, 997, the disclosures of which are incorporated by reference herein.

Non-limiting examples of cationic polymers include:

(1) homo- and co-polymers derived from at least one monomer chosen from acrylic esters, methacrylic esters and amides, wherein said homo- and co-polymers comprise at least one unit chosen from units of formulae:

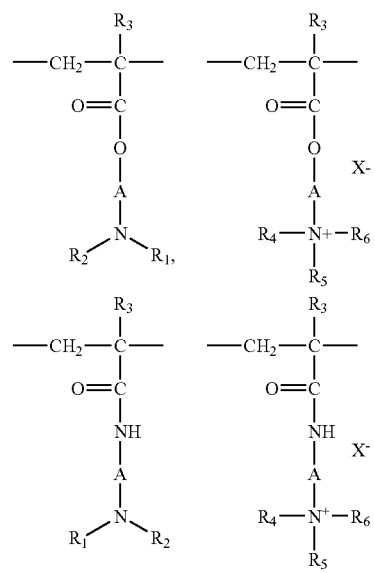

wherein:

$R_3$, which may be identical or different, are each chosen from hydrogen atoms and $CH_3$ groups;

A, which may be identical or different, are each chosen from linear and branched alkyl groups comprising from 1 to 6 carbon atoms, such as 2 and 3 carbon atoms, and hydroxyalkyl groups comprising from 1 to 4 carbon atoms;

$R_4$, $R_5$ and $R_6$, which may be identical or different, are each chosen from alkyl groups comprising from 1 to 18 carbon atoms, such as from 1 to 6 carbon atoms, and benzyl groups;

$R_1$ and $R_2$, which may be identical or different, are each chosen from hydrogen atoms and alkyl groups comprising from 1 to 6 carbon atoms, such as methyl and ethyl;

$X^-$ is an anion chosen from anions derived from at least one inorganic acid and anions derived from at least one organic acid, such as methosulfate anions and halides, such as chlorides and bromides.

Copolymers of family (1) may further comprise at least one unit derived from at least one comonomer chosen from vinyllactams, vinyl esters, acrylamides, methacrylamides, diacetone acrylamides, acrylamides and methacrylamides substituted on the nitrogen with at least one group chosen from ($C_1$-$C_4$) alkyls, acrylic acids, methacrylic acids, acrylic esters, and methacrylic esters. Non-limiting examples of vinyllactams include vinylpyrrolidone and vinylcaprolactam.

Non-limiting examples of copolymers of family (1) include:

copolymers derived from at least one monomer of (i) acrylamide and (ii) dimethylaminoethyl methacrylate quaternized with at least one group chosen from dimethyl sulfate and dimethyl halide, such as the product sold under the name HERCOFLOC by the company Hercules;

copolymers derived from at least one monomer of (i) acrylamide and (ii) methacryloyloxy-ethyltrimethylammonium chloride described, for example, in patent application EP-A-080 976, the disclosure of which is incorporated herein by reference, and which is sold under the name BINA QUAT P 100 by the company Ciba Geigy;

copolymers derived from at least one monomer of (i) acrylamide and (ii) methacryloyloxy-ethyltrimethylammonium methosulfate, such as, for example, copolymers sold under the name RETEN by the company Hercules;

quaternized and non-quaternized vinylpyrrolidone/dialkylaminoalkyl acrylate copolymers and quaternized and non-quaternized vinylpyrrolidone/dialkylaminoalkyl methacrylate copolymers, such as the products sold under the name "GAFQUAT" by the company ISP, such as, for example, "GAFQUAT 734" or "GAFQUAT 755" and the products known as "COPOLYMER 845, 958 and 937". These polymers are described in detail in French patents 2 077 143 and 2 393 573, the disclosures of which are incorporated herein by reference;

dimethylaminoethyl methacrylate/vinylcaprolactam/vinylpyrrolidone terpolymers, such as the product sold under the name GAFFIX VC 713 by the company ISP;

vinylpyrrolidone/methacrylamidopropyldimethylamine copolymers, such as the product sold under the name STYLEZE CC 10 by ISP; and quaternized vinylpyrrolidone/dimethylaminopropylmethacrylamide copolymers, such as the product sold under the name "GAFQUAT HS 100" by the company ISP;

(2) cellulose ether derivatives comprising quaternary ammonium groups, such as those described in French patent 1,492,597, the disclosure of which is incorporated herein by reference, and polymers sold under the names "JR" (JR 400, JR 125 and JR 30M) and "LR" (LR 400, or LR 30M) by the company Union Carbide Corporation. These polymers are also defined in the CTFA dictionary as quaternary ammoniums of hydroxyethylcellulose which have reacted with an epoxide substituted with a trimethylammonium group;

(3) cationic cellulose derivatives such as cellulose copolymers and cellulose derivatives grafted with at least one water-soluble monomer of quaternary ammonium, such as those described in U.S. Pat. No. 4,131,576, the disclosure of which is incorporated herein by reference, such as hydroxyalkylcelluloses (such as, for example, hydroxymethylcelluloses, hydroxyethylcelluloses and hydroxypropylcelluloses, wherein said hydroxyalkylcelluloses are grafted with at least one salt chosen from, for example, methacryloylethyltrimethylammonium salts, methacrylamidopropyltrimethylammonium salts and dimethyldiallylammonium salts). For example, commercial products corresponding to the aforementioned cationic cellulose derivatives include the products sold under the names "CELQUAT L 200" and "CELQUAT H 100" by the company National Starch;

(4) cationic polysaccharides, such as those described in U.S. Pat. Nos. 3,589,578 and 4,031,307, the disclosures of which are incorporated herein by reference, such as guar gums comprising at least one cationic trialkylammonium group. For example, guar gums modified with at least one salt, such as a chloride salt, of 2,3-epoxypropyltrimethylammonium may be used in the present invention. Such products are sold in particular under the trade names JAGUAR C13 S, JAGUAR C 15, JAGUAR C 17 and JAGUAR C162 by the company Meyhall;

(5) polymers comprising (i) at least one piperazinyl unit and (ii) at least one group chosen from divalent alkylene groups and divalent hydroxyalkylene groups, wherein said at least one group optionally comprises at least one chain chosen from straight chains and branched chains, wherein said at least one chain is optionally interrupted by at least one entity chosen from oxygen atoms, sulfur atoms, nitrogen atoms, aromatic rings and heterocyclic rings, the oxidation products of said polymers and the quaternization products of said polymers. For example, such polymers are described in French patents 2,162,025 and 2,280,361, the disclosures of which are incorporated herein by reference;

(6) water-soluble polyamino amides which may be prepared by at least one polycondensation reaction of at least one acidic compound and at least one polyamine compound, wherein said polyamino amides may be crosslinked with at least one crosslinking agent chosen from epihalohydrins, diepoxides, dianhydrides, unsaturated dianhydrides, bis-unsaturated derivatives, bis-halohydrins, bis-azetidiniums, bis-haloacyldiamines, bis-alkyl halides and oligomers derived from reaction of at least one difunctional compound with at least one compound chosen from bis-halohydrins, bis-azetidiniums, bis-haloacyidiamines, bis-alkyl halides, epihalohydrins, diepoxides and bis-unsaturated derivatives, wherein said crosslinking agent may be used in a proportion generally ranging from 0.025 mol to 0.35 mol per amine group of said polyamino amide, wherein said polyamino amides may optionally be alkylated, and wherein if said polyamino amides comprise at least one tertiary amine group, said polyamino amides may optionally be quaternized. For example, such polymers are described in French patents 2,252,840

(7) polyamino amide derivatives derived from condensation of at least one polyalkylene polyamine with at least one polycarboxylic acid, followed by alkylation with at least one bifunctional agent. Non-limiting examples of such polyamino amide derivatives include adipic acid/dialkylaminohydroxyalkyldialkylenetriamine polymers wherein the alkyl group comprises from 1 to 4 carbon atoms, such as methyl groups, ethyl groups and propyl groups. For example, such polymers are described in French patent 1,583,363, the disclosure of which is incorporated herein by reference.

Other non-limiting examples of such derivatives include the adipic acid/dimethylaminohydroxypropyl/diethylenetriamine polymers sold under the name "CARTARETINE F, F4 or F8" by the company Sandoz.

(8) polymers derived from the reaction of (i) at least one polyalkylene polyamine comprising two primary amine groups and at least one secondary amine group with (ii) at least one dicarboxylic acid chosen from diglycolic acid and saturated aliphatic dicarboxylic acids comprising from 3 to 8 carbon atoms. According to the present invention, the molar ratio of the at least one polyalkylene polyamine to the at least one dicarboxylic acid generally ranges from 0.8:1 to 1.4:1. The polyamino amide resulting from the above reaction may be reacted with epichlorohydrin in a molar ratio of epichlorohydrin to the at least one secondary amine group of the polyamino amide generally ranging from 0.5:1 to 1.8:1. For example, such polymers are described in U.S. Pat. Nos. 3,227,615 and 2,961,347, the disclosures of which are incorporated herein by reference.

Polymers of this type are sold in particular under the name "HERCOSETT 57" by the company Hercules Inc. and under the name "PD 170" or "DELSETTE 101" by the company Hercules in the case of adipic acid/epoxypropyl/diethylenetriamine copolymers.

(9) cyclopolymers of alkyldiallylamine and cyclopolymers of dialkyldiallylammonium, such as homopolymers and copolymers comprising, as a constituent of the chain, at least one unit chosen from units of formulae (VI) and (VI'):

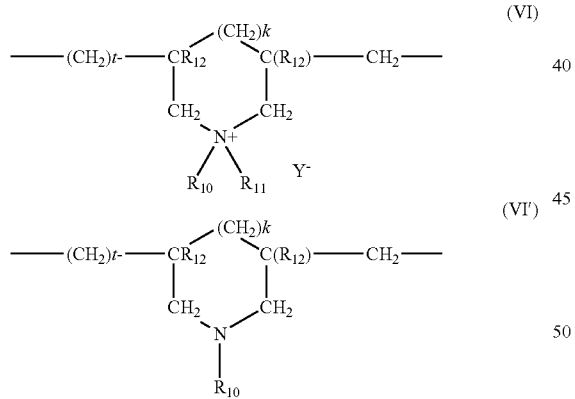

wherein:
  k and t, which may be identical or different, are each chosen from 0 and 1, with the proviso that the sum of k+t is equal to 1;
  $R_{12}$, which may be identical or different, are each chosen from hydrogen atoms and methyl groups;
  $R_{10}$ and $R_{11}$, which may be identical or different, are each chosen from alkyl groups comprising from 1 to 22 carbon atoms, such as from 1 to 4 carbon atoms, hydroxyalkyl groups, such as hydroxy alkyl groups wherein the alkyl radical comprises from 1 to 5 carbon atoms, and $C_1$-$C_4$ amidoalkyl groups;

$R_{10}$ and $R_{11}$, together with the nitrogen atom to which they are commonly bonded, may additionally form at least one heterocyclic group, such as piperidyl groups and morpholinyl groups;

$Y^-$ is an anion, such as bromide, chloride, acetate, borate, citrate, tartrate, bisulfate, bisulfite, sulfate and phosphate. For example, such polymers are described in French patent 2,080,759 and in its Certificate of Addition 2,190,406, the disclosures of which are incorporated herein by reference.

Non-limiting examples of the polymers defined above include the dimethyldiallyl-ammonium chloride homopolymer sold under the name "MERQUAT 100" by the company Calgon (and its homologues of low weight-average molecular mass) and copolymers of diallyidimethylammonium chloride and of acrylamide, sold under the name "MERQUAT 550".

(10) quaternary diammonium polymers comprising repeating units of formula (VII):

wherein:
  $R_{13}$, $R_{14}$, $R_{15}$ and $R_{16}$, which may be identical or different, are each chosen from aliphatic groups comprising from 1 to 20 carbon atoms, alicyclic groups comprising from 2 to 20 carbon atoms, arylaliphatic groups comprising from 5 to 20 carbon atoms, and lower hydroxyalkyl groups; and
  additionally at least two of said $R_{13}$, $R_{14}$, $R_{15}$ and $R_{16}$, together with the nitrogen atoms to which they are attached, may form at least one heterocycle optionally comprising an additional heteroatom other than nitrogen; and
  additionally, $R_{13}$, $R_{14}$, $R_{15}$ and $R_{16}$, which may be identical or different, may each be chosen from linear and branched $C_1$-$C_6$ alkyl groups substituted with at least one group chosen from nitrile groups, ester groups, acyl groups, amide groups and groups chosen from groups of formulae —CO—O—$R_{17}$-D and —CO—NH—$R_{17}$-D wherein $R_{17}$ is chosen from alkylene groups and D is chosen from quaternary ammonium groups;
  $A_1$ and $B_1$, which may be identical or different, are each chosen from polymethylene groups comprising from 2 to 20 carbon atoms, chosen from linear and branched, saturated and unsaturated polymethylene groups wherein said polymethylene groups may optionally comprise, optionally linked to and optionally intercalated in the main chain, at least one entity chosen from aromatic rings, oxygen atoms, sulfur atoms, sulfoxide groups, sulfone groups, disulfide groups, amino groups, alkylamino groups, hydroxyl groups, quaternary ammonium groups, ureido groups, amide groups and ester groups; and
  $X^-$ is an anion chosen from anions derived from inorganic acids and anions derived from organic acids; and
  $A_1$, $R_{13}$ and $R_{15}$ may optionally form, together with the nitrogen atoms to which they are attached, at least one piperazine ring;
  with the proviso that if $A_1$ is chosen from linear and branched, saturated and unsaturated alkylene groups and linear and branched, saturated and unsaturated hydroxyalkylene groups, $B_1$ may also be chosen from groups of formula:

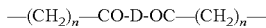

wherein:
n is a number such that the overall quaternary diammonium polymer has a number-average molecular mass generally ranging for example from 1000 to 100,000;

n and p, which may be identical or different, are each chosen from integers ranging from 2 to 20; and $X^-$ is an anion chosen from anions derived from inorganic acids and anions derived from organic acids.

(11) polyquaternary ammonium polymers comprising repeating units of formula (VIII):

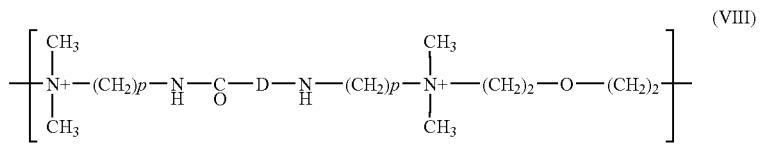

D is chosen from:
a) glycol residues of formula: —O-Z-O—, wherein Z is chosen from linear and branched hydrocarbon groups and groups chosen from groups of formulae:

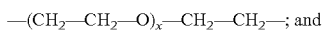

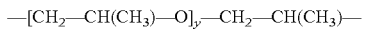

wherein x and y, which may be identical or different, are each chosen from integers ranging from 1 to 4 (in which case x and y represent a defined and unique degree of polymerization) and any number ranging from 1 to 4 (in which case x and y represent an average degree of polymerization);

b) bis-secondary diamine residues such as piperazine derivatives;

c) bis-primary diamine residues chosen from residues of formula: —NH—Y—NH—, wherein Y is chosen from linear and branched hydrocarbon groups and residues of formula —$CH_2$—$CH_2$—S—S—$CH_2$—$CH_2$—; and d) ureylene groups of formula: —NH—CO—NH—.

In one embodiment, $X^-$ is an anion chosen from chloride ions and bromide ions. According to the present invention, the quarternary diammonium polymers have a number-average molecular mass generally ranging from 1000 to 100,000.

For example, polymers of this type are described in French Patent Nos. 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020, the disclosures of which are incorporated herein by reference.

Further, according to the present invention, polymers comprising repeating units of formula (a) may be used:

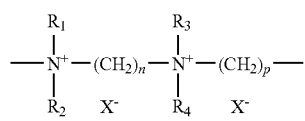

wherein:
$R_1$, $R_2$, $R_3$ and $R_4$, which may be identical or different, are each chosen from alkyl groups comprising from 1 to 4 carbon atoms and hydroxyalkyl groups comprising from 1 to 4 carbon atoms;

wherein:
p is an integer ranging from 1 to 6,
D is chosen from direct bonds and —$(CH_2)_r$—CO— groups, wherein r is a number equal to 4 or 7, and
$X^-$ is an anion chosen from anions derived from inorganic acids and anions derived from organic acids.

For example, such compounds are described in patent application EP-A-122,324, the disclosure of which is incorporated by reference herein, and may be prepared according to the procedures described in the U.S. Pat. Nos. 4,157,388, 4,390,689, 4,702,906, and 4,719,282, the disclosures of which are incorporated by reference herein.

Among these, there may be mentioned for example the products "Mirapol A 15", "Mirapol AD1", "Mirapol AZ1" and "Mirapol 175" sold by the company Miranol.

(12) quaternary polymers of vinylpyrrolidone and quaternary polymers of vinylimidazole, such as, for example, the products sold under the names LUVIQUAT FC 905, FC 550 and FC 370 by the company BASF.

(13) polyamines, such as POLYQUART H sold by Henkel under the reference name "POLYETHYLENE GLYCOL (15) TALLOW POLYAMINE" in the CTFA dictionary.

(14) crosslinked (meth)acryloyloxy($C_1$-$C_4$)alkyltri($C_1$-$C_4$)alkylammonium salt polymers, such as the polymers derived from homopolymerization of dimethylaminoethyl methacrylate quaternized with methyl chloride and polymers derived from copolymerization, for example, of acrylamide with dimethylaminoethyl methacrylate quaternized with a methyl halide (such as methyl chloride), wherein the homo- or copolymerization is followed by crosslinking with at least one compound comprising olefinic unsaturation, such as methylenebisacrylamide. For example, a crosslinked acrylamide/methacryloyloxyethyltrimethylammonium chloride copolymer (20/80 by weight) in the form of a dispersion comprising about 50% by weight of said copolymer in mineral oil may be used. This dispersion is sold under the name "SALCARE SC 92" by the company Allied Colloids. Further, a crosslinked methacryloyloxyethyltrimethylammonium chloride homopolymer comprising about 50% by weight of the homopolymer in mineral oil or in a liquid ester may be used. These dispersions are sold under the names "SALCARE SC 95" and "SALCARE SC 96" by the company Allied Colloids.

Other cationic polymers which may be used as the at least one cationic polymer according to the present invention are polyalkyleneimines (such as polyethyleneimines), polymers comprising at least one vinylpyridine unit, polymers comprising at least one vinylpyridinium unit, condensates of polyamines, condensates of epichlorohydrin, quaternary polyureylenes and chitin derivatives.

Other embodiments of the invention use cationic polymers chosen from the polymers of (1), (9), (10), (11) and (14). Specifically, polymers of formulae (W) and (U) can be used:

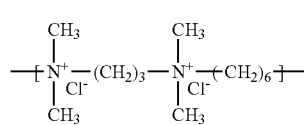

(W)

such as those of which the molecular weight, determined by gel chromatography, ranges from 9500 to 9900;

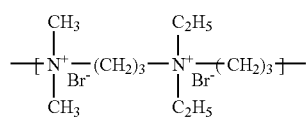

(U)

and in particular those of which the molecular weight, determined by gel chromatography, is approximately 1200.

Generally, the cationic polymers are present in an amount ranging for example from 0.01% to 10% by weight relative to the total weight of the final composition, such as from 0.05% to 5% by weight relative to the total weight of the final composition, and further such as from 0.1% to 3% by weight relative to the total weight of the final composition.

Amphoteric Polymers

The amphoteric polymers which can be used in the present invention can be chosen from polymers comprising K and M units distributed statistically in the polymer chain, wherein:

K is a unit derived from a monomer comprising at least one basic nitrogen atom and M is a unit derived from an acid monomer comprising at least one group chosen from carboxylic groups and sulfonic groups; or alternatively K and M, which are identical or different, are each groups chosen from groups derived from zwitterionic monomers of carboxybetaines and groups derived from zwitterionic monomers of sulfobetaines; or alternatively K and M, which are identical or different, are each chosen from polymers comprising cationic polymer chains comprising at least one amine group chosen from primary, secondary, tertiary and quaternary amine groups, wherein at least one of the amine groups is substituted with a group chosen from carboxylic groups and sulphonic groups linked via a hydrocarbon radical; or alternatively K and M form part of a chain of a polymer with an α,β-dicarboxylic ethylene unit wherein one of the carboxylic groups has been caused to react with a polyamine comprising at least one amine group chosen from primary amine groups and secondary amine groups.

Representative of the film forming amphoteric polymers defined above that can be used include the following polymers:

(1) The polymers resulting from the copolymerization of a monomer derived from a vinyl compound substituted with a carboxylic group such as acrylic acid, methacrylic acid, maleic acid, and α-chloroacrylic acid, and of a basic monomer derived from a substituted vinyl compound comprising at least one basic atom such as dialkylaminoalkyl methacrylate and acrylate, dialkylaminoalkylmethacrylamide and acrylamide. Such compounds are described in U.S. Pat. No. 3,836,537, the disclosure of which is incorporated by reference herein. Copolymer of the sodium acrylate/acrylamidopropyl-trimethylammonium chloride sold under the name of "POLYQUART KE 3033" by the company HENKEL can also be cited.

The vinyl compound can also be a salt of dialkyldiallylammonium such as dimethyldiallylammonium chloride. The copolymers of acrylic acid and the latter monomer are proposed under the name "MERQUAT 280", "MERQUAT 295" and "MERQUAT PLUS 3330" by the company CALGON.

(2) The polymers comprising units derived from:
a) at least one monomer chosen from acrylamides substituted on the nitrogen by an alkyl radical and methacrylamides substituted on the nitrogen by an alkyl radical,
b) at least one acidic comonomer comprising at least one reactive carboxylic group, and
c) at least one basic comonomer such as comonomers chosen from esters of acrylic acid and esters of methacrylic acid, said esters being substituted with at least one amine chosen from primary, secondary, tertiary and quaternary amines, and the product of quaternization of dimethylaminoethyl methacrylate with a sulfate chosen from dimethyl sulfate and diethyl sulfate.

Some embodiments according to the invention utilize N-substituted acrylamides and methacrylamides comprising $(C_2-C_{12})$alkyl groups, such as N-ethylacrylamide, N-tert-butylacrylamide, N-tert-octylacrylamide, N-octylacrylamide, N-decylacrylamide, and N-dodecylacrylamide, as well as the corresponding methacrylamides.

The acidic comonomers can be chosen, for example, from acrylic, methacrylic, crotonic, itaconic, maleic and fumaric acids as well as the $(C_1-C_4)$alkyl monoesters of entities chosen from maleic anhydride, fumaric anhydride, maleic acid, and fumaric acid.

The basic comonomers can be chosen, for example, from methacrylates of aminoethyl, butylaminoethyl, N,N'-dimethylaminoethyl, and N-tert-butylaminoethyl.

Additionally, the copolymers having the CTFA name (4$^{th}$ edition, 1991) Octylacrylamide/acrylates/butylaminoethyl-methacrylate copolymer such as the products sold under the name AMPHOMER and LOVOCRYL 47 by the company NATIONAL STARCH can also be used.

(3) The partially and completely alkylated and crosslinked polyaminoamides derived from polyaminoamides of formula:

(VIII)

wherein:

$R_{27}$ is a divalent group chosen from groups derived from saturated dicarboxylic acids, groups derived from dicarboxylic aromatic acids, groups derived from mono- and dicarbocylic aliphatic acids comprising at least one ethylenic double bond, groups derived from an ester of $(C_1-C_6)$alkanols of said acids, and groups derived from the addition of any one of said aforementioned acids with an amine chosen from bis-primary and bis-secondary amines, and Z is a divalent group derived from polyalkylene-polyamines chosen from bis-primary, mono- and bis-secondary polyalkylene-polyamines, for example, Z represents:

a) in an amount ranging from 60 mol % to 100 mol %, the group

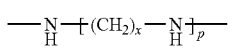 (IX)

wherein x=2 and p=2 or 3, or alternatively x=3 and p=2,
it being understood that group Z of formula a) is derived from a compound chosen from diethylenetriamine, triethylenetetraamine and dipropylenetriamine;

b) in an amount ranging from 0 mol % to 40 mol %, (1) said groups (IX) above in which x=2 and p=1 and which said group is derived from a compound chosen from ethylenediamine, and (2) groups derived from piperazine:

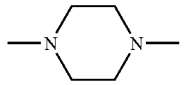

c) in an amount ranging from 0 mol % to 20 mol %, the polyalkylene-polyamine group —NH—(CH$_2$)$_6$—NH—, which is derived from hexamethylenediamine, wherein said polyalkylene-polyamine group is crosslinked by adding a bifunctional crosslinking agent (chosen from the epihalohydrins, diepoxides, dianhydrides, and bis-unsaturated derivatives) present in an amount ranging from 0.025 mol to 0.35 mol of crosslinking agent per amine group of the polyamino amide and alkylated by the action of at least one compound chosen from acrylic acid, chloroacetic acid, alkanesultones, and salts thereof.

The saturated dicarboxylic acids are for example chosen from saturated ($C_6$-$C_{10}$) dicarboxylic acids such as adipic, 2,2,4-trimethyladipic and 2,4,4-trimethyladipic acid.

Representative dicarboxylic aromatic acids include for example ($C_6$-$C_{10}$) dicarboxylic aromatic acids, such as terephthalic acid. And representative mono- and dicarboxylic aliphatic acids comprising at least one ethylenic double bond include for example acrylic, methacrylic and itaconic acids.

The alkanesultones used in the alkylation can, for example, be chosen from propanesultone and butanesultone, and the salts of the alkylating agents can be chosen from sodium and potassium salts of said alkylating agents.

(4) The polymers comprising zwitterionic units of formula:

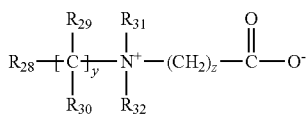 (X)

wherein:
$R_{28}$ is chosen from polymerizable unsaturated groups such as acrylate, methacrylate, acrylamide and methacrylamide groups,
y and z, which can be identical or different, are each chosen from integers ranging from 1 to 3,
$R_{29}$ and $R_{30}$, which may be identical or different, are each chosen from hydrogen, and methyl, ethyl and propyl groups,
$R_{31}$ and $R_{32}$, which may be identical or different, are each chosen from hydrogen and alkyl groups, provided that the sum of the carbon atoms in $R_{31}$ and $R_{32}$ does not exceed 10.

The polymers comprising such units may also comprise units derived from nonzwitterionic monomers such as dimethylaminoethyl acrylate, dimethylaminoethyl methacrylate, diethylaminoethyl acrylate, diethylaminoethyl methacrylate, alkyl acrylates, alkyl methacrylates, alkyl acrylamides, alkyl methacrylamides, and vinyl acetate.

By way of example, there may be mentioned the copolymer of methyl methacrylate/methyl dimethylcarboxymethylammonioethyl methacrylate such as the product sold under the name DIAFORMER Z301 by the company SANDOZ.

(5) The polymers derived from chitosan comprising at least one monomeric unit chosen from formulae (D), (E) and (F), which are described for example in U.S. Pat. No. 4,996,059, the disclosure of which is herein incorporated by reference:

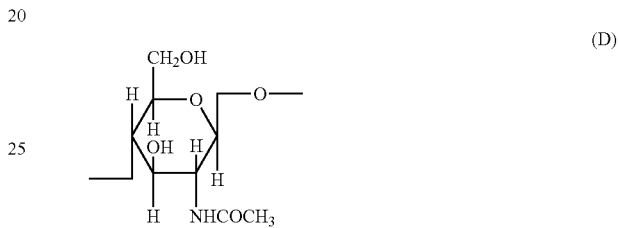 (D)

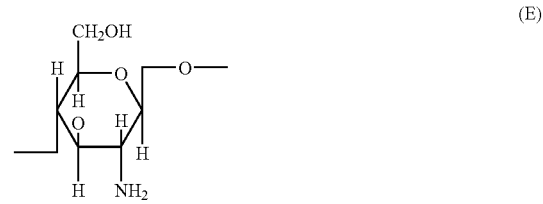 (E)

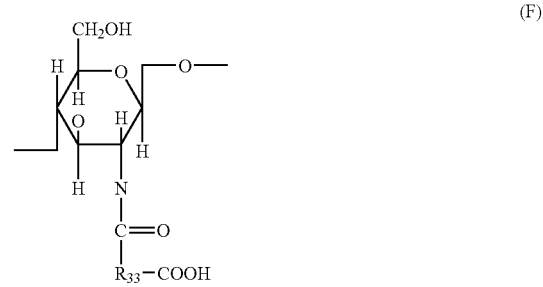 (F)

wherein said unit (D) is present in an amount ranging for example from 0% to 30%, by weight relative to the total weight of said polymer, said unit (E) is present in an amount ranging for example from 5% to 50% by weight relative to the total weight of said polymer, and said unit (F) is present in an amount ranging for example from 30% to 90% by weight relative to the total weight of said polymer,
and wherein in said unit (F), $R_{33}$ is chosen from groups of formula:

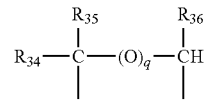

wherein:
q is equal to 0 or 1, and (i) when q is equal to 0, $R_{34}$, $R_{35}$ and $R_{36}$, which may be identical or different, are each chosen from:

hydrogen, methyl, hydroxyl, acetoxy, and amino groups, monoalkylamine and dialkylamine groups optionally interrupted by at least one nitrogen atom and/or optionally substituted with at least one group chosen from amine, hydroxyl, carboxyl, alkylthio and sulfonic groups, and alkylthio groups wherein said alkyl portion of said alkylthio group carries an amino group, provided that at least one of said $R_{34}$, $R_{35}$ and $R_{36}$ groups is chosen from hydrogen; and (ii) when q is equal to 1, $R_{34}$, $R_{35}$ and $R_{36}$, which may be identical or different, are each chosen from hydrogen, and the salts formed by these polymers (5) with bases, and the salts formed by these polymers (5) with acids.

(6) The polymers derived from the N-carboxyalkylation of chitosan such as N-carboxymethyl chitosan and N-carboxybutyl chitosan sold under the name "EVALSAN" by the company JAN DEKKER.

(7) The polymers of formula (XI), which are described for example in French Patent 1 400366, the disclosure of which is incorporated by reference herein:

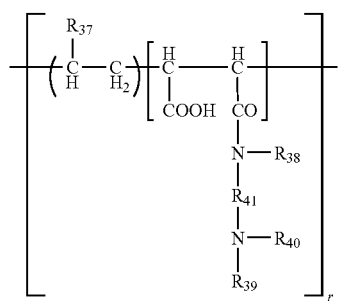

(XI)

wherein:
r is chosen such that the number-average molecular weight of said polymer ranges from 500 to 6,000,000, such as from 1000 to 1,000,000.

$R_{37}$ is chosen from hydrogen and $CH_3O$, $CH_3CH_2O$, and phenyl groups, $R_{38}$ and $R_{39}$, which are identical or different, are each chosen from hydrogen and lower alkyl groups such as methyl and ethyl, $R_{40}$ is chosen from lower alkyl groups such as methyl and ethyl and groups of formula: —$R_{41}$—$N(R_{39})_2$, comprising up to 6 carbon atoms, wherein $R_{39}$ is as defined above and $R_{41}$ is defined below, $R_{41}$ is chosen from —$CH_2$—$CH_2$—, —$CH_2$—$CH_2$—$CH_2$—, and —$CH_2$—$CH(CH_3)$—.

(8) Amphoteric polymers of the -D-X-D-X— type, which are described for example in U.S. Pat. No. 4,996,059, the disclosure of which is herein incorporated by reference, chosen from:

a) polymers derived from reaction of chloroacetic acid or sodium chloroacetate with at least one compound comprising at least one unit of formula (XII):

-D-X-D-X-D- (XII)

wherein D is a group:

and X is chosen from the symbols E and E', wherein E and E', which are identical or different, are each chosen from bivalent groups chosen from alkylene groups comprising at least one chain chosen from linear and branched chains comprising up to 7 carbon atoms in the principal chain, wherein said principal chain is optionally substituted with at least one hydroxyl group, and wherein said alkylene groups optionally comprise at least one atom chosen from oxygen atoms, nitrogen atoms and sulfur atoms, wherein said at least one optional atom is present in the form of at least one group chosen from ether, thioether, sulfoxide, sulfone, sulfonium, alkylamine and alkenylamine groups, and hydroxyl, benzylamine, amine oxide, quaternary ammonium, amide, imide, alcohol, ester and urethane groups, and wherein said alkylene groups optionally comprise from 1 to 3 rings chosen from aromatic rings and heterocyclic rings, b) polymers of formula:

-D-X-D-X— (XIII)

wherein:
D is a group:

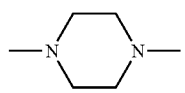

X is chosen from the symbols E and E' and wherein at least one X is chosen from E', E is chosen from bivalent groups chosen from alkylene groups comprising at least one chain chosen from linear and branched chains comprising up to 7 carbon atoms in the principal chain, wherein said alkylene groups are optionally substituted with at least one hydroxyl group, and wherein said alkylene groups optionally comprise at least one atom chosen from oxygen atoms, nitrogen atoms, and sulfur atoms, wherein said at least one optional atom is present in the form of at least one group chosen from ether, thioether, sulfoxide, sulfone, sulfonium, alkylamine and alkenylamine groups, and hydroxyl, benzylamine, amine oxide, quaternary ammonium, amide, imide, alcohol, ester and urethane groups, and wherein said alkylene groups optionally comprises 1 to 3 rings chosen from aromatic rings and heterocyclic rings, and E' is a bivalent group chosen from alkylene groups comprising at least one chain chosen from linear and branched chains comprising up to 7 carbon atoms in the principal chain, wherein said principal chain is optionally substituted with at least one hydroxyl group, and wherein said alkylene groups comprise at least one nitrogen atom substituted with an alkyl chain, wherein said alkyl chain is optionally interrupted by an oxygen atom and, wherein said alkyl chain comprises at least one functional group chosen from carboxyl and hydroxyl functional groups, and wherein said at least one alkyl chain is betainized by reaction with a reactant chosen from chloroacetic acid and sodium chloroacetate.

(9) The copolymers ($C_1$-$C_5$)alkyl vinyl ether/maleic anhydride partially modified by semiamidation with an N,N-dialkylaminoalkylamine such as N,N-dimethylaminopropylamine or by semiesterification with an N,N-dialkanolamine. These copolymers may also comprise other vinyl comonomers such as vinylcaprolactam.

The amphoteric polymers of family (1) are utilized in certain embodiments of the invention.

According to the invention, the at least one polymer chosen from cationic and amphoteric polymers may be present in an amount ranging for example from 0.01% to 10% by weight relative to the total weight of the composition, such as from 0.05% to 5% by weight relative to the total weight of the composition, and further such as from 0.1% to 3% by weight relative to the total weight of the composition.

Surfactants

The ready-to-use composition according to the invention can comprise at least one surfactant, which is present in at least one of said at least one dyeing composition (A), said at least one oxidizing composition (B), and said at least one dyeing composition (A) and said at least one oxidizing composition (B).

The at least one surfactant may be chosen from anionic, amphoteric, nonionic, zwitterionic and cationic surfactants.

Representative choices for the at least one surfactant include the following:

(i) Anionic Surfactant(s):

Representative anionic surfactants include salts (for example alkaline salts, such as sodium salts, ammonium salts, amine salts, amino alcohol salts and magnesium salts) of the following compounds: alkyl sulfates, alkyl ether sulfates, alkylamidoether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; alkyl($C_6$-$C_{24}$) sulfosuccinates, alkyl($C_6$-$C_{24}$) ether sulfosuccinates, alkyl($C_6$-$C_{24}$)amide sulfosuccinates, alkylsulfosuccinamates alkyl($C_6$-$C_{24}$) sulfoacetates, acyl($C_6$-$C_{24}$) sarcosinates, acyl($C_6$-$C_{24}$) glutamates, acyl isethionates, N-acyltaurates, and alkyl($C_6$-$C_{24}$) polyglycoside carboxylic esters such as alkylglucoside citrates, alkylpolyglycoside tartrate, alkylpolyglycoside sulfosuccinates, and alkyl sulfosuccinamates. The alkyl and acyl radicals of all of these various compounds can for example comprise from 12 to 20 carbon atoms, and the aryl radicals can for example be chosen from phenyl and benzyl groups.

For example, anionic surfactants can be chosen from fatty acid salts such as the salts of oleic acid, ricinoleic acid, palmitic acid, stearic acid, the acids of copra oil and the acids of hydrogenated copra oil, and acyl lactylates in which the acyl radical comprises from 8 to 20 carbon atoms. At least one weakly anionic surfactant can also be used, such as alkyl-D-galactosideuronic acids and their salts, as well as polyoxyalkylenated carboxylic ($C_6$-$C_{24}$)alkyl ether acids, polyoxyalkylenated carboxylic ($C_6$-$C_{24}$)alkylaryl ether acids, polyoxyalkylenated carboxylic ($C_6$-$C_{24}$)alkyl amidoether acids and their salts, for example, those comprising from 2 to 50 ethylene oxide groups.

(ii) Nonionic Surfactant(s):

Useful nonionic surfactants include compounds that are well known per se (see for example in this respect "Handbook of Surfactants" by M. R. Porter, published by Blackie & Son (Glasgow and London), 1991, pp. 116-178), the disclosure of which is incorporated by reference herein. Thus, nonionic surfactants can include alcohols, α-diols, and polyethoxylated alkylphenols and polypropoxylated alkylphenols comprising at least one fatty chain comprising for example from 8 to 18 carbon atoms, wherein the number of ethylene oxide and propylene oxide groups can range for example from 2 to 50. Additionally, copolymers of ethylene oxide, copolymers of propylene oxide, condensates of ethylene oxide with fatty alcohols, condensates of propylene oxide with fatty alcohols, polyethoxylated fatty amides, such as those comprising from 2 to 30 mol of ethylene oxide, polyglycerolated fatty amides on average comprising 1 to 5 glycerol groups, such as from 1.5 to 4, polyethoxylated fatty amines comprising for example from 2 to 30 mol of ethylene oxide, oxyethylenated fatty acid esters of sorbitan comprising from 2 to 30 mol of ethylene oxide, fatty acid esters of sucrose, fatty acid esters of polyethylene glycol, alkylpolyglycosides, N-alkylglucamine derivatives, amine oxides, such as the oxides of ($C_{10}$-$C_{14}$) alkylamines, and N-acylaminopropylmorpholine oxides can also be used. It will be noted that the alkylpolyglycosides are nonionic surfactants that can be suitable in the context of the present invention.

(iii) Amphoteric or Zwitterionic Surfactant(s):

Representative amphoteric and zwitterionic surfactants can be chosen from aliphatic secondary and tertiary amine derivatives in which the aliphatic radical is chosen from linear and branched chain radicals comprising 8 to 18 carbon atoms and comprising at least one water-soluble anionic group (chosen for example from carboxylate, sulfonate, sulfate, phosphate and phosphonate); mention may also be made of ($C_8$-$C_{20}$)alkylbetaines, sulfobetaines, ($C_8$-$C_{20}$)alkylamido($C_1$-$C_6$)alkylbetaines and ($C_8$-$C_{20}$)alkylamido($C_1$-$C_6$) alkylsulfobetaines.

Representative amine derivatives include the products sold under the name MIRANOL, as described in U.S. Pat. Nos. 2,528,378 and 2,781,354, the disclosures of which are incorporated by reference herein, and classified in the CTFA dictionary, 3$^{rd}$ edition, 1982, under the names Amphocarboxyglycinates and Amphocarboxypropionates, having the respective structures:

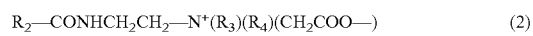

$$R_2\text{—CONHCH}_2\text{CH}_2\text{—N}^+(R_3)(R_4)(CH_2COO\text{—}) \quad (2)$$

in which:
- $R_2$ is chosen from alkyl groups derived from an acid $R_2$—COOH present in hydrolysed copra oil, and heptyl, nonyl and undecyl radicals,
- $R_3$ is a beta-hydroxyethyl group, and
- $R_4$ is a carboxymethyl group;

and

$$R_5\text{—CONHCH}_2\text{CH}_2\text{—N(B)(C)} \quad (3)$$

in which:
- (B) is —$CH_2CH_2OX'$, wherein X' is an entity chosen from a —$CH_2CH_2$—COOH group and a hydrogen atom,
- (C) is —$(CH_2)_z$—Y', wherein z=1 or 2, and wherein Y' is an entity chosen from —COOH and —$CH_2$—CHOH—$SO_3H$ groups,
- $R_5$ is chosen from alkyl groups, such as (a) alkyl groups of an acid $R_5$—COOH present in oils chosen from copra oil and hydrolysed linseed oil, (b) alkyl groups, such as $C_7$, $C_9$, $C_{11}$ and $C_{13}$ alkyl groups, and (c) $C_{17}$ alkyl groups and the iso forms, and unsaturated $C_{17}$ groups.

Such representative compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid. By way of example, mention may be made of the cocoamphodiacetate sold under the trade name MIRANOL C2M Concentrate by the company RHODIA CHIMIE.

(iv) Cationic Surfactants:

Representative cationic surfactants include salts of optionally polyoxyalkylenated primary, secondary and tertiary fatty amines; quaternary ammonium salts such as tetraalkylammonium, alkylamidoalkyltrialkylammonium, trialkylbenzylammonium, and trialkylhydroxyalkylammonium, alkylpyridinium chlorides, alkylpyridinium bromides, imidazoline derivatives; and amine oxides of cationic nature.

The at least one surfactant may be present in the composition according to the invention generally in an amount ranging for example from 0.01% to 40% by weight relative to the total weight of the composition, such as from 0.1% to 30% by weight relative to the total weight of the composition.

The ready-to-use composition according to the present invention may eventually comprise, in composition (A), composition (B), or both compositions (A) and (B), at least one other agent for adjustment of rheology, such as agents chosen from cellulose thickeners (for example, hydroxyethylcellulose, hydroxypropylcellulose, and carboxymethylcellulose), guar gum and its derivatives (for example, hydroxypropylguar), gums of microbial origin (for example, xanthan gum and scieroglucan gum), and synthetic thickeners not having a fatty chain (for example, crosslinked homopolymers of acrylic acid and crosslinked homopolymers of acrylamidopropanesulfonic acid).

Generally, these thickeners may be present in an amount ranging for example from 0.01% to 10% by weight relative to the total weight of the composition.

The medium of the composition appropriate for dyeing can be an aqueous medium, optionally comprising at least one cosmetically acceptable organic solvent.

Representative organic solvents may be chosen from alcohols, such as ethyl alcohol, isopropyl alcohol, benzyl alcohol, and phenylethyl alcohol. The organic solvents may also be chosen from glycols (for example, ethyleneglycol, propyleneglycol, butyleneglycol, dipropyleneglycol, and diethyleneglycol) and ethers of glycols (for example, monomethyl, monoethyl and monobutyl ethers of ethyleneglycol and for example monomethyl ether of propyleneglycol and alkyl ethers of diethyleneglycol glycol, such as, for example, monoethylether and monobutylether of diethyleneglycol).

The organic solvents are generally present in an amount ranging for example from 0.5% to 20% by weight relative to the total weight of the composition, such as from 2% to 10% by weight relative to the total weight of the composition.

The composition according to the invention may further comprise an effective quantity of other agents. For example, agents that are already known for oxidation coloration, such as various ordinary adjuvants including sequesterizers such as EDTA and etidronic acid, UV-screening agents, waxes, volatile and nonvolatile, cyclic and non-cyclic, linear and branched, organomodified (such as by amine groups) silicones, preservatives, ceramides, pseudoceramides, vegetable, mineral and synthetic oils, vitamins and provitamins such as panthenol, and opacifiers, may be included.

The composition can also comprise at least one agent chosen from reducing agents and antioxidants. Representative additional agents may include sodium sulfite, thioglycolic acid, thiolactic acid, sodium bisulfite, dehydroascorbic acid, hydroquinone, 2-methylhydroquinone, tert-butylhydroquinone and homogentisic acid. Generally, such agents may be present in the an amount ranging for example from 0.05% to 3% by weight relative to the total weight of the composition, such as from 0.05% to 1.5% by weight relative to the total weight of the composition.

The composition according to the invention may also comprise at least one fatty alcohol. The at least one fatty alcohol includes, but is not limited to, fatty alcohols chosen from fatty alcohols, and mixtures of fatty alcohols. The expression fatty alcohols includes, but is not limited to, linear and branched, saturated and unsaturated fatty alcohols. Representative fatty alcohols may be used include lauryl, cetyl, stearyl and oleyl alcohols. The at least one fatty alcohol may be present in an amount ranging for example from 0.001% to 20% by weight relative to the total weight of the composition.

One skilled in the art should take care to select said optionally complementary compounds, such that the advantageous properties intrinsically associated with the dye composition according to the invention are not, or are not substantially, adversely affected by the additions envisaged.

In the ready-to-use composition, said at least one composition (B) may comprise at least one oxidizing agent chosen, for example, from hydrogen peroxide, urea peroxide, alkali metal bromates and ferricyanides, and persalts such as perborates and persulfates. More specifically, hydrogen peroxide may be used. This oxidizing agent is advantageously constituted by an oxygenated aqueous solution of which the titre may range from 1 to 40 in volume, such as from 5 to 40.

As an oxidizing agent, at least one oxidation-reduction enzyme such as laccases, peroxydases and 2-electron oxydoreductases (such as uricase), if necessary in the presence of their respective donor or cofactor, may also be used.

The pH of the dyeing composition (A) or of the ready-to-use composition applied to the keratin fibers [composition resulting from combining the dye composition (A) and the oxidizing composition (B)], generally ranges from 4 to 12, such as from 6 to 11, and may be adjusted to the desired value by means of at least one agent chosen from acidifying and basifying agents well-known in the art of dyeing keratin fibers.

Representative basifying agents include aqueous ammonia, alkali metal carbonates, alkanolamines such as mono-, di- and triethanolamines and derivatives thereof, hydroxyalkylamines and oxyethylenated and oxypropylenated ethylenediamines, sodium and potassium hydroxide and compounds of formula (XIV):

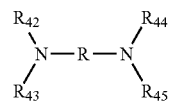

(XIV)

wherein:
R is a propylene residue optionally substituted with a group chosen from hydroxyl and $C_1$-$C_4$ alkyl groups;
$R_{42}$, $R_{43}$, $R_{44}$ and $R_{45}$, which may be identical or different, are each chosen from hydrogen, $C_1$-$C_4$ alkyl groups and $C_1$-$C_4$ hydroxyalkyl groups.

Representative acidifying agents include, classically, by way of example, organic and inorganic acids such as hydrochloric acid, orthophosphoric acid, and carboxylic acids such as tartaric acid, citric acid, lactic acid and sulfonic acids.

One dyeing method according to the invention comprises applying on dry or wet keratin fibers, such as human keratin fibers like hair, at least one ready-to-use cosmetic composition, prepared at the time of use from at least one composition (A) and at least one composition (B), leaving said at least one ready-to-use composition on said keratin fibers for a time ranging from 1 to 60 minutes, such as from 10 to 45 minutes, rinsing said keratin fibers, optionally shampooing said keratin fibers, rinsing said keratin fibers after said optional shampooing, and drying said keratin fibers, wherein said at least one ready-to-use cosmetic composition comprises:

at least one composition (A) comprising, in a dyeing medium:
(1) at least one oxidation dye,
(2) at least one thickening polymer comprising at least one fatty chain, and
(3) at least one fatty alcohol chosen from monoglycerolated and polyglycerolated fatty alcohols, and
at least one composition (B) comprising at least one oxidizing agent.

Another process comprises applying on dry or wet keratin fibers, such as human keratin fibers like hair, at least one ready-to-use cosmetic composition, prepared at the time of use from at least one composition (A'), at least one composition (A"), and at least one composition (B), leaving said at least one ready-to-use composition on said keratin fibers for a resting time ranging from 1 to 60 minutes, such as from 10 to 45 minutes, rinsing said keratin fibers, optionally shampooing said keratin fibers, and after said optional shampooing again rinsing and drying said keratin fibers, wherein said composition comprises:

at least one composition (A') comprising at least one oxidation dye and at least one fatty alcohol chosen from monoglycerolated and polyglycerolated fatty alcohols,
at least one composition (A") comprising at least one thickening polymer comprising at least one fatty chain,
at least one composition (B) comprising at least one oxidizing agent, and
wherein said composition comprising said at least one compositions (A'), (A") and (B) is prepared by combining said at least one compositions (A'), (A"), and (B) at the moment of use.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Concrete examples illustrating the invention are indicated below without however exhibiting a limiting character.

EXAMPLES

The following compositions were prepared:

Oxidizing Composition:

| | |
|---|---|
| Fatty alcohol | 2.3 g |
| Oxyethylenated fatty alcohol | 0.6 g |
| Fatty amide | 0.9 g |
| Glycerin | 0.5 g |
| Hydrogen peroxide | 7.5 g |
| Perfume | qs |
| Demineralized water qs | 100 g |

Dyeing Composition:

| | (expressed in grams) |
|---|---|
| Mixture of C18 to C24 linear alcohols [C18/C20/C22/C24, 7/58/30/6] (NAFOL 20-22) | 3 |
| Mixture of polyglycerolated C18 to C24 linear alcohols [C18/C20/C22/C24, 7/58/30/6] containing 6 mol of glycerol | 1.35 |
| Polyglycerolated cetearyl alcohol containing 2 mol of glycerol | 4 |
| Polyglycerolated cetearyl alcohol containing 6 mol of glycerol | 2 |
| Oleic acid | 2.6 |
| Glycol distearate | 2 |
| Propylene glycol | 5 |
| Monoisopropanolamide of copra acids | 2 |
| Aculyn 44 sold by the company ROHM & HAAS | 1.4 AS* |
| Crosslinked polyacrylic acid | 0.6 |
| Cationic polymer of formula (W) | 3 AS* |
| Merquat 100 sold by the company CALGON | 0.4 AS* |
| Reducing agents | 0.7 |
| Seqestrants | 0.2 |
| 1,3-Dihydroxybenzene (resorcinol) | 0.6 |
| 1,4-Diaminobenzene | 0.5 |
| 1-Hydroxy-3-aminobenzene | 0.1 |
| 1-Hydroxy-2-aminobenzene | 0.05 |
| 1-Hydroxy-4-aminobenzene | 0.09 |
| 6-Hydroxybenzomorpholine | 0.017 |
| 1-b-Hydroxyethyloxy-2,4-diaminobenzene, dihydrochloride | 0.039 |
| Propylene glycol monobutyl ether | 2.5 |
| Pure monoethanolamine | 1.06 |
| Aqueous ammonia (containing 20.5% of ammonia) | 11.1 |
| Water qs | 100 |

AS* = Active Substance

The dyeing composition was combined, at the time of use, in a plastic bowl and for 2 minutes, with the oxidizing composition given above, in an amount of 1 part of dyeing composition per 1.5 parts of oxidizing composition. The mixture obtained was applied to locks of natural grey hair which is 90% white and allowed to act for 30 minutes. The locks were then rinsed with water, they were washed with shampoo and again rinsed with water, and then dried and disentangled. The hair was then dyed in an intense light chestnut brown shade.

Results of the same type were obtained by replacing, in the above example, Aculyn 44 with 0.5% AS of Quatrisoft LM 200 sold by the company AMERCHOL or with 0.5% AS of Pure Thix HH sold by the company SUD CHEMIE.

What is claimed is:

1. A cosmetic composition for oxidation dyeing keratin fibers, comprising, in a dyeing medium
   (1) at least one oxidation dye,
   (2) at least one thickening polymer comprising at least one fatty chain chosen from:
       anionic thickening polymers comprising at least one hydrophilic unit of the olefinic unsaturated carboxylic acid type and at least one ($C_{10}$-$C_{30}$)alkyl ester of unsaturated carboxylic acid type;
       nonionic thickening polymers chosen from celluloses modified by at least one group comprising at least one fatty chain and polyether-polyurethanes comprising in their chain at least one hydrophilic polyoxyethylenated sequence and at least one hydrophobic sequence chosen from aliphatic chains, cycloaliphatic chains and aromatic chains; and
       cationic thickening polymers wherein the fatty chain is a quaternized cellulose derivative; and
   (3) at least one fatty alcohol chosen from monoglycerolated and polyglycerolated fatty alcohols.

2. A composition according to claim 1, wherein said keratin fibers are chosen from human keratin fibers.

3. A composition according to claim 2, wherein said human keratin fibers are chosen from human hair.

4. A composition according to claim 1, wherein said at least one fatty alcohol is chosen from fatty alcohols of formula:

RO—(—CH$_2$—CH(CH$_2$—OH)—O—)$_n$—H in which:
R is chosen from linear and branched, saturated and unsaturated groups comprising from 8 to 40 carbon atoms; and
n is a number ranging from 1 to 30.

5. A composition according to claim 4, wherein said R comprises from 10 to 30 carbon atoms.

6. A composition according to claim 4, wherein said n is a number ranging from 1 to 10.

7. A composition according to claim 1, wherein said at least one fatty alcohol chosen from monoglycerolated and polyglycerolated fatty alcohols is present in an amount ranging from 0.01% to 30% by weight relative to the total weight of the composition.

8. A composition according to claim 7, wherein said at least one fatty alcohol chosen from monoglycerolated and polyglycerolated fatty alcohols is present in an amount ranging from 0.05% to 20% by weight relative to the total weight of the composition.

9. A composition according to claim 8, wherein said at least one fatty alcohol chosen from monoglycerolated and polyglycerolated fatty alcohols is present in an amount ranging from 0.1% to 15% by weight relative to the total weight of the composition.

10. A composition according to claim 1, wherein said at least one hydrophilic unit of the olefinic unsaturated carboxylic acid type is chosen from monomeric residues formed from monomers of formula (II):

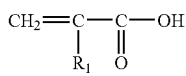

(II)

in which R$_1$ is chosen from H, CH$_3$, and C$_2$H$_5$, and wherein at least one hydrophobic unit of the ($C_{10}$-$C_{30}$)alkyl ester of unsaturated carboxylic acid type is chosen from monomeric residues formed from monomers of formula (III):

(III)

in which R$_2$ is chosen from H, CH$_3$, and C$_2$H$_5$, and R$_3$ is chosen from $C_{10}$-$C_{30}$ alkyl groups.

11. A composition according to claim 10, wherein said R$_3$ is chosen from $C_{12}$-$C_{22}$ alkyl groups.

12. A composition according to claim 1, wherein said anionic thickening polymers comprising at least one fatty chain are chosen from copolymers formed from at least two monomers, wherein at least one of said at least two monomers is chosen from a carboxylic acid with α,β-monoethylenic unsaturation, an ester of a carboxylic acid with α,β-monoethylenic unsaturation, and an oxyalkylenated fatty alcohol.

13. A composition according to claim 1, wherein said nonionic thickening polymers are chosen from polyether-polyurethanes comprising at least two lipophilic hydrocarbon chains, comprising from 6 to 30 carbon atoms, separated by a hydrophilic sequence, wherein said hydrocarbon chains are chosen from pendant chains and chains at the end of a hydrophilic sequence.

14. A composition according to claim 1, wherein said nonionic thickening polymers are chosen from polyether-polyurethanes comprising a polyblock sequence.

15. A composition according to claim 14, wherein said polyether-polyurethanes are in tri-block form.

16. A composition according to claim 1, wherein said at least one thickening polymer comprising at least one fatty chain is present in an amount ranging from 0.01% to 10% by weight relative to the total weight of the composition.

17. A composition according to claim 16, wherein said at least one thickening polymer comprising at least one fatty chain is present in an amount ranging from 0.1% to 5% by weight relative to the total weight of the composition.

18. A composition according to claim 1, wherein said at least one oxidation dye is chosen from oxidation bases, oxidation couplers, and their acid addition salts.

19. A composition according to claim 1, wherein said at least one oxidation dye is chosen from oxidation bases.

20. A composition according to claim 19, wherein said oxidation bases are chosen from ortho- and para-phenylenediamines, double bases, ortho- and para-aminophenols, heterocyclic bases, and acid addition salts of any of the foregoing.

21. A composition according to claim 20, wherein said para-phenylenediamines are chosen from compounds of formula (I):

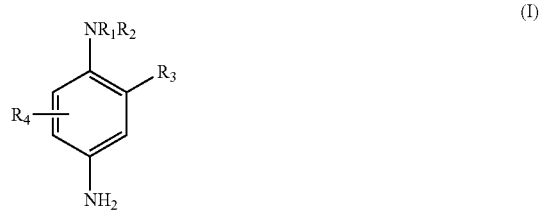

(I)

wherein:
- $R_1$ is chosen from hydrogen, $C_1$-$C_4$ alkyl groups, monohydroxy($C_1$-$C_4$ alkyl) groups, polyhydroxy($C_2$-$C_4$ alkyl) groups, ($C_1$-$C_4$)alkoxy($C_1$-$C_4$)alkyl groups, phenyl groups, 4'-aminophenyl groups, and $C_1$-$C_4$ alkyl groups substituted with at least one group chosen from nitrogen-containing groups,
- $R_2$ is chosen from hydrogen, $C_1$-$C_4$ alkyl groups, monohydroxy($C_1$-$C_4$ alkyl) groups, polyhydroxy($C_2$-$C_4$ alkyl) groups, ($C_1$-$C_4$)alkoxy($C_1$-$C_4$)alkyl groups, and $C_1$-$C_4$ alkyl groups substituted with a nitrogen-containing group;
- $R_1$ and $R_2$ may also form, together with the nitrogen atom to which they are bonded, a 5- to 6-membered nitrogen-containing heterocycle ring, optionally substituted with at least one group chosen from alkyl groups, hydroxyl groups and ureido groups;
- $R_3$ is chosen from hydrogen, halogens, $C_1$-$C_4$ alkyl groups, sulfo groups, carboxyl groups, monohydroxy($C_1$-$C_4$ alkyl) groups, hydroxy($C_1$-$C_4$ alkyoxy) groups, acetylamino($C_1$-$C_4$ alkoxy) groups, mesylamino($C_1$-$C_4$ alkoxy) groups, and carbamoylamino($C_1$-$C_4$ alkoxy) groups; and
- $R_4$ is chosen from hydrogen, halogens, and $C_1$-$C_4$ alkyl groups.

22. A composition according to claim 21, wherein said $R_3$ is chlorine.

23. A composition according to claim 20, wherein said double bases are chosen from compounds of formula (II):

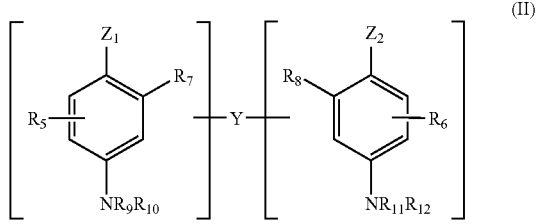

(II)

wherein:
- $Z_1$ and $Z_2$, which may be identical or different, are each chosen from hydroxyl groups, and —$NH_2$ groups, optionally substituted with a group chosen from $C_1$-$C_4$ alkyl groups, and linkers Y;
- linker Y is chosen from linear and branched, divalent alkylene groups comprising from 1 to 14 carbon atoms, optionally interrupted by, or optionally terminating with, at least one entity chosen from nitrogen-containing groups and heteroatoms, and optionally substituted with at least one group chosen from hydroxyl groups, and $C_1$-$C_6$ alkoxy groups;
- $R_5$ and $R_6$, which may be identical or different, are each chosen from hydrogen, halogens, $C_1$-$C_4$ alkyl groups, monohydroxy($C_1$-$C_4$ alkyl) groups, polyhydroxy($C_2$-$C_4$ alkyl) groups, amino($C_1$-$C_4$ alkyl) groups, and linkers Y; and
- $R_7$, $R_8$, $R_9$, $R_{10}$, $R_{11}$ and $R_{12}$, which may be identical or different, are each chosen from hydrogen, linkers Y, and $C_1$-$C_4$ alkyl groups;
- provided that said compounds of formula (II) comprise only one linker Y per molecule.

24. A composition according to claim 23, wherein said heteroatoms are chosen from oxygen, sulfur, and nitrogen.

25. A composition according to claim 21, wherein said nitrogen-containing groups are chosen from amino, mono ($C_1$-$C_4$)alkylamino, ($C_1$-$C_4$)dialkylamino, ($C_1$-$C_4$)trialkylamino, monohydroxy($C_1$-$C_4$)alkylamino, imidazolinium, and ammonium radicals.

26. A composition according to claim 23, wherein said nitrogen-containing groups are chosen from amino, mono ($C_1$-$C_4$)alkylamino, ($C_1$-$C_4$)dialkylamino, ($C_1$-$C_4$)trialkylamino, monohydroxy($C_1$-$C_4$)alkylamino, imidazolinium, and ammonium radicals.

27. A composition according to claim 20, wherein said para-aminophenols are chosen from compounds of formula (III):

(III)

wherein:
- $R_{13}$ is chosen from hydrogen, halogens, $C_1$-$C_4$ alkyl groups, monohydroxy($C_1$-$C_4$ alkyl) groups, ($C_1$-$C_4$) alkoxy($C_1$-$C_4$)alkyl groups, amino($C_1$-$C_4$ alkyl), and hydroxy($C_1$-$C_4$)alkylamino($C_1$-$C_4$ alkyl) groups; and
- $R_{14}$ is chosen from hydrogen, halogens, $C_1$-$C_4$ alkyl groups, monohydroxy($C_1$-$C_4$ alkyl) groups, polyhydroxy($C_2$-$C_4$ alkyl) groups, amino($C_1$-$C_4$ alkyl) groups, cyano($C_1$-$C_4$ alkyl) groups, and ($C_1$-$C_4$)alkoxy($C_1$-$C_4$) alkyl groups.

28. A composition according to claim 27, wherein said halogens are fluorine.

29. A composition according to claim 20, wherein said heterocyclic bases are chosen from pyridine derivatives, pyrimidine derivatives, pyrazolopyrimidine derivatives, and pyrazole derivatives.

30. A composition according to claim 19, wherein said oxidation bases are present in an amount ranging from 0.0005% to 12% by weight relative to the total weight of the composition.

31. A composition according to claim 18, wherein said oxidation couplers are chosen from meta-phenylenediamines, meta-aminophenols, meta-diphenols, heterocyclic couplers, and their acid addition salts.

32. A composition according to claim 18, wherein said oxidation couplers are present in an amount ranging from 0.0001% to 10% by weight relative to the total weight of the composition.

33. A composition according to claim 18, wherein said acid addition salts are chosen from hydrochlorides, hydrobromides, sulfates, tartrates, lactates, and acetates.

34. A composition according to claim 1 further comprising at least one direct dye.

35. A composition according to claim 1 further comprising at least one reducing agent.

36. A composition according to claim 35, wherein said at least one reducing agent is present in an amount ranging from 0.05% to 3% by weight relative to the total weight of the composition.

37. A composition according to claim 1 further comprising at least one additional fatty alcohol.

38. A composition according to claim 37, wherein said at least one additional fatty alcohol is present in an amount ranging from 0.001% to 20% by weight relative to the total weight of the composition.

39. A ready-to-use cosmetic composition for oxidation dyeing keratin fibers, wherein said ready-to-use cosmetic composition is obtained by combining at least one composition (A), in a dyeing medium, comprising:
at least one oxidation dye,
at least one thickening polymer comprising at least one fatty chain chosen from:
anionic thickening polymers comprising at least one hydrophilic unit of the olefinic unsaturated carboxylic acid type and at least one ($C_{10}$-$C_{30}$)alkyl ester of the unsaturated carboxylic acid type;
nonionic thickening polymers chosen from celluloses modified by at least one group comprising at least one fatty chain and polyether-polyurethanes comprising in their chain at least one hydrophilic polyoxyethylenated sequence and at least one hydrophobic sequence chosen from aliphatic chains, cycloaliphatic chains and aromatic chains; and
cationic thickening polymers wherein the fatty chain is a quaternized cellulose derivative, and
at least one fatty alcohol chosen from monoglycerolated and polyglycerolated fatty alcohols, with at least one composition (B) comprising at least one oxidizing agent.

40. A composition according to claim 39, wherein said at least one oxidizing agent is chosen from hydrogen peroxide, urea peroxide, alkali metal bromates, alkali metal ferricyanides, persalts, and oxidation-reduction enzymes.

41. A composition according to claim 40, wherein said oxidation-reduction enzymes are chosen from laccases, peroxidases, and oxidoreductases comprising 2 electrons.

42. A composition according to claim 40, wherein said at least one oxidizing agent is hydrogen peroxide.

43. A composition according to claim 42, wherein said hydrogen peroxide is present in an oxygenated water solution comprising a titre ranging from 1 to 40 in volume.

44. A composition according to claim , wherein said composition possesses a pH ranging from 4 to 12.

45. A composition according to claim 39, wherein said keratin fibers are chosen from human keratin fibers.

46. A composition according to claim 45, wherein said human keratin fibers are chosen from human hair.

47. A cosmetic composition according to claim 39 further comprising at least one polymer chosen from cationic polymers and amphoteric polymers, wherein said at least one polymer is present in said at least one composition (A), in said at least one composition (B), or in said at least one composition (A) and said at least one composition (B).

48. A composition according to claim 47, wherein said at least one polymer is chosen from cationic polymers chosen from quaternary polyammoniums comprising recurring units of formula (W):

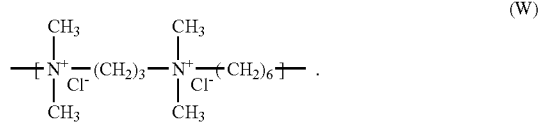

49. A composition according to claim 47, wherein said at least one polymer is chosen from cationic polymers chosen from quaternary polyammoniums comprising recurring units of formula (U):

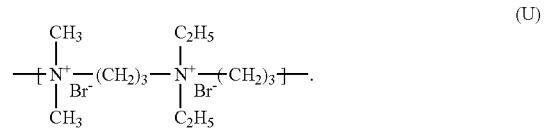

50. A composition according to claim 47, wherein said at least one polymer is chosen from amphoteric polymers chosen from copolymers comprising at least one monomeric residue chosen from acrylic acid residue and a residue of a salt of dimethyldiallylammonium.

51. A composition according to claim 47, wherein said at least one polymer chosen from cationic polymers and amphoteric polymers is present in an amount ranging from 0.01% to 10% by weight relative to the total weight of the composition.

52. A composition according to claim 51, wherein said at least one polymer chosen from cationic polymers and amphoteric polymers is present in an amount ranging from 0.05% to 5% by weight relative to the total weight of the composition.

53. A composition according to claim 52, wherein said at least one polymer chosen from cationic polymers and amphoteric polymers is present in an amount ranging from 0.1% to 3% by weight relative to the total weight of the composition.

54. A composition according to claim 39 further comprising at least one surfactant chosen from anionic, cationic, nonionic and amphoteric surfactants, wherein said at least one surfactant is present in said at least one composition (A), in said at least one composition (B), or in said at least one composition (A) and said at least one composition (B).

55. A composition according to claim 54, wherein said at least one surfactant is present in an amount ranging from 0.01% to 40% by weight relative to the total weight of the composition.

56. A composition according to claim 55, wherein said at least one surfactant is present in an amount ranging from 0.1% to 30% by weight relative to the total weight of the composition.

57. A composition according to claim 39 further comprising at least one thickening agent chosen from cellulose derivatives, guar derivatives, gums of microbial origin, and synthetic thickeners which do not possess a fatty chain, wherein said at least one thickening agent is present in said at least one composition (A), in said at least one composition (B), or in said at least one composition (A) and said at least one composition (B).

58. A composition according to claim 57, wherein said at least one thickening agent is present in an amount ranging from 0.01% to 10% by weight relative to the total weight of the composition.

59. A method for oxidation dyeing keratin fibers comprising:
(a) applying to said keratin fibers at least one composition (A) comprising, in a dyeing medium:
at least one oxidation dye,
at least one thickening polymer comprising at least one fatty chain chosen from:
anionic thickening polymers comprising at least one hydrophilic unit of the olefinic unsaturated carboxylic acid type and at least one ($C_{10}$-$C_{30}$)alkyl ester of the unsaturated carboxylic acid type;

nonionic thickening polymers chosen from celluloses modified by at least one group comprising at least one fatty chain and polyether-polyurethanes comprising in their chain at least one hydrophilic polyoxyethylenated sequence and at least one hydrophobic sequence chosen from aliphatic chains, cycloaliphatic chains and aromatic chains; and cationic thickening polymers wherein the fatty chain is a quaternized cellulose derivative, and at least one fatty alcohol chosen from monoglycerolated or polyglycerolated fatty alcohols; and (b) developing the color with the aid of at least one oxidizing composition (B) comprising at least one oxidizing agent, wherein said at least one oxidizing composition (B) is combined at the time of use with said at least one composition (A) or said at least one oxidizing composition (B) is applied sequentially to said at least one composition (A) without intermediate rinsing.

60. A method according to claim 59, wherein said keratin fibers are chosen from human keratin fibers.

61. A method according to claim 60, wherein said human keratin fibers are human hair.

62. A method for oxidation dyeing keratin fibers comprising:

applying to said keratin fibers at least one cosmetic dyeing composition comprising, in a dyeing medium, at least one oxidation dye and at least one fatty alcohol chosen from monoglycerolated and polyglycerolated fatty alcohols, and optionally comprising at least one thickening polymer comprising at least one fatty chain chosen from:

anionic thickening polymers comprising at least one hydrophilic unit of the olefinic unsaturated carboxylic acid type and at least one $C_{10}$-$C_{30}$)alkyl ester of the unsaturated carboxylic acid type;

nonionic thickening polymers chosen from celluloses modified by at least one group comprising at least one fatty chain and polyether-polyurethanes comprising in their chain at least one hydrophilic polyoxyethylenated sequence and at least one hydrophobic sequence chosen from aliphatic chains, cycloaliphatic chains and aromatic chains; and cationic thickening polymers wherein the fatty chain is a quaternized cellulose derivative, developing the color with the aid of at least one oxidizing composition comprising at least one oxidizing agent and an effective quantity of at least one thickening polymer comprising at least one fatty chain, wherein said at least one oxidizing composition is combined at the time of use with said at least one dyeing composition or wherein said at least one oxidizing composition is applied sequentially to said at least one dyeing composition without intermediate rinsing.

63. A method according to claim 62, wherein said keratin fibers are chosen from human keratin fibers.

64. A method according to claim 63, wherein said human keratin fibers are human hair.

65. A kit for dyeing keratin fibers comprising at least two compartments wherein:

a first compartment comprises (1) at least one oxidation dye, (2) at least one thickening polymer comprising at least one fatty chain chosen from:

anionic thickening polymers comprising at least one hydrophilic unit of the olefinic unsaturated carboxylic acid type and at least one $(C_{10}$-$C_{30})$alkyl ester of the unsaturated carboxylic acid type;

nonionic thickening polymers chosen from celluloses modified by at least one group comprising at least one fatty chain and polyether-polyurethanes comprising in their chain at least one hydrophilic polyoxyethylenated sequence and at least one hydrophobic sequence chosen from aliphatic chains, cycloaliphatic chains and aromatic chains; and cationic thickening polymers wherein the fatty chain is a quaternized cellulose derivative, and (3) at least one fatty alcohol chosen from monoglycerolated and polyglycerolated fatty alcohols, and a second compartment comprises at least one oxidizing agent.

66. A kit according to claim 65, wherein said keratin fibers are chosen from human keratin fibers.

67. A kit according to claim 66, wherein said human keratin fibers are human hair.

68. A kit for dyeing keratin fibers comprising at least two compartments wherein:

a first compartment comprises at least one oxidation dye and at least one fatty alcohol chosen from monoglycerolated and polyglycerolated fatty alcohols, and optionally comprises at least one thickening polymer comprising at least one fatty chain chosen from:

anionic thickening polymers comprising at least one hydrophilic unit of the olefinic unsaturated carboxylic acid type and at least one $(C_{10}$-$C_{30})$alkyl ester of the unsaturated carboxylic acid type;

nonionic thickening polymers chosen from celluloses modified by at least one group comprising at least one fatty chain and polyether-polyurethanes comprising in their chain at least one hydrophilic polyoxyethylenated sequence and at least one hydrophobic sequence chosen from aliphatic chains, cycloaliphatic chains and aromatic chains; and cationic thickening polymers wherein the fatty chain is a quaternized cellulose derivative and a second compartment comprises at least one oxidizing agent and an effective quantity of at least one thickening polymer comprising at least one fatty chain.

69. A kit according to claim 68, wherein said keratin fibers are chosen from human keratin fibers.

70. A kit according to claim 69, wherein said human keratin fibers are human hair.

71. A kit for dyeing keratin fibers comprising at least three compartments wherein:

a first compartment comprises at least one oxidation dye and at least one fatty alcohol chosen from monoglycerolated and polyglycerolated fatty alcohols, and optionally comprises at least one thickening polymer comprising at least one fatty chain chosen from:

anionic thickening polymers comprising at least one hydrophilic unit of the olefinic unsaturated carboxylic acid type and at least one $(C_{10}$-$C_{30})$alkyl ester of the unsaturated carboxylic acid type;

nonionic thickening polymers chosen from celluloses modified by at least one group comprising at least one fatty chain and polyether-polyurethanes comprising in their chain at least one hydrophilic polyoxyethylenated sequence and at least one hydrophobic sequence chosen from aliphatic chains, cycloaliphatic chains and aromatic chains; and cationic thickening polymers wherein the fatty chain is a quaternized cellulose derivative, a second compartment comprises at least one thickening polymer comprising at least one fatty chain chosen from:

anionic thickening polymers comprising at least one hydrophilic unit of the olefinic unsaturated carboxylic acid type and at least one ($C_{10}$-$C_{30}$)alkyl ester of the unsaturated carboxylic acid type;

nonionic thickening polymers chosen from celluloses modified by at least one group comprising at least one fatty chain and polyether-polyurethanes comprising in their chain at least one hydrophilic polyoxyethylenated sequence and at least one hydrophobic sequence chosen from aliphatic chains, cycloaliphatic chains and aromatic chains; and cationic thickening polymers wherein the fatty chain is a quaternized cellulose derivative, and a third compartment comprises at least one oxidizing agent and optionally comprises at least one thickening polymer comprising at least one fatty chain chosen from:

anionic thickening polymers comprising at least one hydrophilic unit of the olefinic unsaturated carboxylic acid type and at least one ($C_{10}$-$C_{30}$)alkyl ester of unsaturated carboxylic acid type;

nonionic thickening polymers chosen from celluloses modified by at least one group comprising at least one fatty chain and polyether-polyurethanes comprising in their chain at least one hydrophilic polyoxyethylenated sequence and at least one hydrophobic sequence chosen from aliphatic chains, cycloaliphatic chains and aromatic chains; and cationic thickening polymers wherein the fatty chain is a quaternized cellulose derivative.

72. A kit according to claim 71, wherein said keratin fibers are chosen from human keratin fibers.

73. A kit according to claim 72, wherein said human keratin fibers are human hair.

74. A composition according to claim 37, wherein said at least one fatty alcohol is chosen from linear and branched, saturated and unsaturated fatty alcohols.

\* \* \* \* \*